(12) United States Patent
Croce et al.

(10) Patent No.: US 9,394,543 B2
(45) Date of Patent: Jul. 19, 2016

(54) MATERIALS AND METHODS RELATED TO MICRORNA-21, MISMATCH REPAIR, AND COLORECTAL CANCER

(71) Applicant: The Ohio State University, Columbus, OH (US)

(72) Inventors: Carlo M. Croce, Columbus, OH (US); Nicola Valeri, Columbus, OH (US)

(73) Assignee: The Ohio State University, Columbus, OH (US)

( * ) Notice: Subject to any disclaimer, the term of this patent is extended or adjusted under 35 U.S.C. 154(b) by 0 days.

(21) Appl. No.: 14/587,356

(22) Filed: Dec. 31, 2014

(65) Prior Publication Data

US 2015/0126585 A1  May 7, 2015

Related U.S. Application Data

(62) Division of application No. 13/884,668, filed as application No. PCT/US2011/060349 on Nov. 11, 2011, now Pat. No. 8,946,187.

(60) Provisional application No. 61/413,180, filed on Nov. 12, 2010.

(51) Int. Cl.

| | |
|---|---|
| *C07H 21/04* | (2006.01) |
| *C12N 15/113* | (2010.01) |
| *A61K 31/513* | (2006.01) |
| *A61K 31/713* | (2006.01) |
| *G01N 33/574* | (2006.01) |
| *A61K 31/7088* | (2006.01) |
| *C12Q 1/68* | (2006.01) |

(52) U.S. Cl.
CPC .......... *C12N 15/1135* (2013.01); *A61K 31/513* (2013.01); *A61K 31/7088* (2013.01); *A61K 31/713* (2013.01); *C12N 15/113* (2013.01); *C12Q 1/6886* (2013.01); *G01N 33/57419* (2013.01); *C12Q 2600/112* (2013.01); *G01N 2800/52* (2013.01); *G01N 2800/56* (2013.01)

(58) Field of Classification Search
None
See application file for complete search history.

(56) References Cited

PUBLICATIONS

Asangani et al., "MicroRNA-21 (miR-21) post-transcriptionally downregulates tumor suppressor Pdcd4 and stimulates invasion, intravasation and metastasis in colorectal cancer", Oncogene, 2008, vol. 27, pp. 2128-2136.

Japanese Notification of Reasons of Rejection, Application No. JP 2013-538930, dated Aug. 28, 2015.

Jover et al., "The efficacy of adjuvant chemotherapy with 5-fluorouracil in colorectal cancer depends on the mismatch repair status", European Journal of Cancer, 2009, vol. 45, pp. 365-373.

Rossi et al., "Modification of miR gene expression pattern in human colon cancer cells following exposure to 5-fluorouracil in vitro", Pharmacological Research, 2007, vol. 56, pp. 248-253.

Yamamichi et al., "Locked Nucleic Acid in situ Hybridization Analysis of miR-21 Expression during Colorectal Cancer Development", Clinical Cancer Research, 2009, vol. 15, pp. 4009-4016.

*Primary Examiner* — Kimberly Chong
(74) *Attorney, Agent, or Firm* — MacMillan, Sobanski & Todd, LLC

(57) ABSTRACT

Described herein is the discovery that miR-21 targets and down-regulates the core mismatch repair (MMR) recognition protein complex hMSH2 and hMSH6. Anti-sense miR-21 is therefore proven as therapeutic herein. Therefore, compositions, kits, therapies and other methods, including methods of treatment/amelioration of symptoms, are disclosed herein.

12 Claims, 14 Drawing Sheets
(14 of 14 Drawing Sheet(s) Filed in Color)

SEQUENCE LISTING

<160> NUMBER OF SEQ ID NOS: 14

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 1
cagaaagccc tggaacttga                                              20

<210> SEQ ID NO 2

```
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
tttccatagt gttaactgtc agtgc                                         25

<210> SEQ ID NO 3
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
cccagtaatg gaatgaaggg tctgtaatag ttttatattg                         40

<210> SEQ ID NO 4
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
aaatgttgct gtgcgccta                                                19

<210> SEQ ID NO 5
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
aaatgttgct gtgcgccta                                                19

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
tcaattgcaa acagtcctca g                                             21

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
tcaattgcaa acagtcctca g                                             21

<210> SEQ ID NO 8
<211> LENGTH: 40
```

-continued

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
caatataaaa ctattacaga cccttcattc cattactggg                            40

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
tagcttttcc tcccccattt                                                  20

<210> SEQ ID NO 10
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
ccacctttgt cagaagtcaa ctc                                              23

<210> SEQ ID NO 11
<211> LENGTH: 26
<212> TYPE: RNA
<213> ORGANISM: Homo sapiens

<400> SEQUENCE: 11
gaaugaaggu aauauugaua agcuau                                           26

<210> SEQ ID NO 12
<211> LENGTH: 22
<212> TYPE: RNA
<213> ORGANISM: Homo sapiens

<400> SEQUENCE: 12
uagcuuauca gacugauguu ga                                               22

<210> SEQ ID NO 13
<211> LENGTH: 24
<212> TYPE: RNA
<213> ORGANISM: Homo sapiens

<400> SEQUENCE: 13
acaacauuau gaucuaauaa acuu                                             24

<210> SEQ ID NO 14
<211> LENGTH: 22
<212> TYPE: RNA
<213> ORGANISM: Homo sapiens

<400> SEQUENCE: 14
uagcuuauca gacugauguu ga                                               22
```

MATERIALS AND METHODS RELATED TO MICRORNA-21, MISMATCH REPAIR, AND COLORECTAL CANCER

CROSS-REFERENCE TO RELATED APPLICATIONS

This application is a divisional application of U.S. Ser. No. 13/884,668 filed Jun. 19, 2013, which claims priority to PCT/2011/060349 filed Nov. 11, 2011, which claims the benefit of U.S. Provisional Application No. 61/413,180, filed Nov. 12, 2010, the disclosures of which are incorporated herein by reference.

SEQUENCE LISTING

The instant application contains a Sequence Listing which has been submitted in ASCII format via EFS-Web and is hereby incorporated by reference in its entirety. Said ASCII copy, created on Nov. 7, 2011, is named 53-52535_SEQ_LIST_OSURF 11085.txt and is 3,139 bytes in size.

FIELD OF THE INVENTION

This invention relates generally to the field of molecular biology. More particularly, it concerns cancer-related technology. Certain aspects of the invention include application in diagnostics, therapeutics, and prognostics of miR-21-associated colorectal cancers. In particular miR21, mismatch repair, and colorectal cancer are discussed herein.

BACKGROUND OF THE INVENTION

Colorectal cancer (CRC) is one of the most frequently occurring cancers in the U.S., with more than 140,000 new cases and about 50,000 deaths expected to occur in 2010. 5-fluorouracil (5-FU) based chemotherapy represents the gold standard for CRC treatment both in the adjuvant and metastatic setting. However, primary or acquired resistance to pyrimidine analog treatments represents a common problem in the management of CRC patients. These observations highlight the need for a better understanding of resistance mechanisms and more effective therapies.

MicroRNAs are a class of small non-coding RNAs that act as post-transcriptional regulators of gene expression and cell homeostasis. Over-expression of miR-21 is a common trait of many solid and hematological malignancies. miR-21 over-expression has been found in blood and stool samples from patients affected by CRC. Moreover, miR-21 over-expression is associated with poor benefit from 5-FU adjuvant chemotherapy in stage II and III CRC.

The Mismatch Repair (MMR) System is involved in DNA damage recognition and repair. hMSH2 and hMLH1 function as core MMR proteins and form heterodimers with protein homologs hMSH3 or hMSH6 and hMLH3 or hPMS2 respectively. Heterodimer formation is fundamental for the DNA damage recognition and represents a crucial step for the stability of the MMR protein homologs. Defects in MMR proteins have been associated with reduced or absent benefit from 5-FU adjuvant chemotherapy in clinical trials. MMR impairment appears to cause reduced incorporation of 5-FU metabolites into DNA leading to reduced G2/M arrest and apoptosis after 5-FU treatment.

The over-expression of miR-21 is linked to a number of human tumors including colorectal cancer, where it appears to regulate the expression of tumor suppressor genes including p21, PTEN, TGFβRII and Bax.

SUMMARY OF THE INVENTION

The present invention demonstrates that miR-21 targets and down-regulates the core mismatch repair (MMR) recognition protein complex hMSH2 and hMSH6. Colorectal tumors that express a high level of miR-21 display reduced hMSH2 protein expression. Cells that overproduce miR-21 exhibit significantly reduced 5-fluorouracil (5-FU) induced G2/M damage arrest and apoptosis that is characteristic of defects in the core MMR component. Moreover, xenograft studies demonstrate that miR-21 over-expression dramatically reduces the therapeutic efficacy of 5-FU. The present studies show that MMR mutator gene down-regulation associated with miR-21 over-expression may be an important clinical indicator of therapeutic efficacy in colorectal cancer.

The present invention provides compositions of matter comprising at least one anti-sense miRNA and at least one additional composition, wherein the anti-sense miRNA is miR-21 and is capable of downregulating at least one core MMR protein, and wherein the at least one additional composition is useful to treat MMR-related disease. Preferably, the at least one additional composition is selected from the group consisting of: a chemotherapy drug; a stem cell; AG1478; gefitinib (Iressa); erlotinib (Tarceva); cetuximab; panitumab; zalutumamab; nimotuzamab; matuzumab; and lapatinib. Preferably, the at last one core MMR protein is selected from the group consisting of: hMSH1; hMSH6; and hMLH1.

The present invention therefore provides compositions of matter comprising antisense miR-21 and 5-flurouracil, or pharmaceutically-acceptable formulations thereof.

Also provided are compositions of matter, comprising antisense miR-21 and means to increase human MutS homolog 2, or pharmaceutically-acceptable formulations thereof.

Also provided are compositions of matter comprising antisense miR-21 and a colorectal cancer treatment compound, or pharmaceutically-acceptable formulations thereof.

Also provided are compositions of matter comprising sense or antisense miR-21 and a pyrimidine analog.

Also provided are compositions of matter wherein the pyrimidine analog is 5-flurorouracil.

The present invention provides kits comprising a composition of claim 4.

Also provided are which further comprises means for identifying hMSH2 expression status.

Also provided are kits wherein the means for identifying hMSH2 expression status is an antibody.

Also provided are kits which further comprise instructions for screening test compounds as potential colorectal cancer treatments.

The present invention provides methods to affect at least one human cell, comprising introducing to at least one hMutSH2-underexpressing cell an underexpression-decreasing amount of antisense miR-21.

Also provided are methods wherein the at least one hMutSH2-underexpressing cell is at least one colorectal cancer cell.

Also provided are methods wherein the at least one hMutSH2-underexpressing cell is present in vitro.

Also provided are methods wherein the at least one hMutSH2-underexpressing cell is present in situ.

Also provided are methods wherein the at least one hMutSH2-underexpressing cell is present in vivo.

Also provided are methods which result in apoptosis of the at least one hMutSH2-underexpressing cell.

Also provided are methods wherein the at least one hMutSH2-underexpressing cell is many cells that form a tumor.

Also provided are methods wherein the tumor is decreased in size after introduction of the antisense miR-21.

Also provided are methods which further comprise introducing 5-flurouracil to the at least one hMutSH2-underexpressing cell.

Also provided are methods which further comprise introducing 5-flurouracil to the at least one hMutSH2-underexpressing cell.

The present invention provides methods to treat a patient with primary or acquired pyrimidine analog-resistant colorectal cancer, comprising administering antisense miR-21 to a patient with primary or acquired pyrimidine analog-resistant colorectal cancer.

Also provided are methods wherein the patient has down-regulated hMSH2.

Also provided are methods which further comprise administering an additional colorectal cancer adjuvant or treatment to the patient.

Also provided are methods which further comprise administering 5-flurouracil to the patient.

Also provided are methods to treat a patient with stage II or stage III colorectal cancer, comprising administering antisense miR-21 to a patient with stage II or stage III colorectal cancer.

Also provided are methods wherein the patient has down-regulated hMSH2.

Also provided are methods which further comprise administering an additional colorectal cancer adjuvant or treatment to the patient.

Also provided are methods which further comprise administering 5-flurouracil to the patient.

The present invention provides methods to treat a patient with colorectal cancer, comprising: a.) identifying if a patient with colorectal cancer has decreased hMSH2 expression, and b.) treating the patient with antisense miR-21 if the patient has decreased hMSH2 expression.

The present invention provides methods to treat a patient with colorectal cancer, comprising: a.) identifying if a patient with colorectal cancer has decreased hMSH2 expression compared to control, and b.) treating the patient with antisense miR-21 if the patient has decreased hMSH2 expression.

The present invention provides methods to treat a patient with colorectal cancer, comprising: a.) identifying if a patient with colorectal cancer has decreased hMSH2 expression compared to control, b.) identifying if the patient with colorectal cancer has increased miR-21 expression compared to control, and c.) treating the patient with antisense miR-21 if the patient has increased miR-21 expression and decreased hMSH2 expression compared to control.

The present invention provides methods to identify useful compounds, comprising: a.) introducing a test compound and antisense and/or sense miR-21 to hMSH2-expressing cells, and b.) identifying test compounds useful to affect hMSH2-expressing cells.

The present invention provides methods to identify cancer cell sample status, comprising: a.) correlating hMSH2 and miR-21 status in a cell test sample with control, and b.) identifying cancer cell sample status.

The present invention provides methods to predict colorectal cancer cell sample status, comprising: a.) correlating hMSH2 and miR-21 status in a colorectal cancer cell-containing test sample with control, and b.) predicting colorectal cancer cell sample status.

The present invention provides methods to identify organism cancer status, comprising: a.) correlating hMSH2 and miR-21 status in an organism-derived test sample with control, and b.) identifying organism status.

The present invention provides methods to predict organism colorectal cancer status, comprising: a.) correlating hMSH2 and miR-21 status in an organism-derived test sample with control, and b.) identifying organism colorectal cancer status.

The present invention provides methods to inhibit G2/M arrest and apoptosis in 5-flurouracil-resistant colorectal cancer cells, comprising introducing to 5-flurouracil-resistant colorectal cancer cells a G2/M arrest and apoptosis-inhibiting amount of antisense miR-21.

The present invention provides methods to inhibit inflammation in 5-flurouracil-resistant colorectal cancer cells, comprising introducing to 5-flurouracil-resistant colorectal cancer cells an inflammation-inhibiting amount of antisense miR-21.

Various aspects of this invention will become apparent to those skilled in the art from the following detailed description of the preferred embodiment, when read in light of the accompanying drawings.

BRIEF DESCRIPTION OF THE DRAWINGS

The patent or application file may contain one or more drawings executed in color and/or one or more photographs. Copies of this patent or patent application publication with color drawing(s) and/or photograph(s) will be provided by the Patent Office upon request and payment of the necessary fee.

FIG. 1A: miR-21 (SEQ ID NOS 12 and 14, respectively) predicted seed regions in hMSH2 (SEQ ID NO: 11) and hMSH6 (SEQ ID NO: 13) 3'UTR are shown.

FIG. 1B: Colo-320DM and SW620 were transiently transfected with miR-21, scrambled-miR, siRNA anti-MSH2 or anti-MSH6 for 48 hours. hMSH2 and hMSH6 mRNA expression was analyzed by Real Time-PCR.

FIG. 1C: Western blotting analysis of miR-21 dependent down-regulation of both hMSH2 and hMSH6. Transfections were similar to (FIG. 1B).

FIGS. 1D, 1E, and 1F HCT-116, SW480 and RKO that contain high endogenous levels of miR-21 cells were transfected with an LNA anti-miR-21 or anti-miR control for 48 hours followed by western blotting analysis of hMSH2 and hMSH6 protein E: hMSH2 and hMSH6 3'UTR were subcloned downstream of the luciferase genes (MSH2-Luc-WT and MSH6-Luc-WT respectively) as well as hMSH2 and hMSH6 3'UTR containing a deletion of the miR-21 target site (MSH2-Luc-mutant and MSH6-Luc-mutant) respectively and co-transfected with miR-21 or scrambled miR. Luciferase activity was recorded after 24 hours. The data represent the mean and S.D from at least 3 determinations from 4 independent transfections. * $p<0.01$.

FIG. 2A: Paraffin-embedded, formalin-fixed CRC tissues were incubated with an LNA-probe anti-miR-21 or scrambled probe as well as IHC antibody against hMSH2. Representative photographs were captured with the Nuance system software. CRC samples where staining was positive for both miR-21 and hMSH2 are shown. Blue and red staining identifies miR-21 and hMSH2 protein respectively.

FIG. 2B: RNA and proteins were extracted from fresh frozen human colorectal tissues. miR-21 expression was assessed by northern blotting, and MMR proteins expression by western blotting in a series of human CRC.

FIG. 5A: Left—Western analysis of hMSH2 protein expression in removed tumors.

FIG. 5A: Right—Tumor growth during and after 5-FU treatment.

FIG. 5B: Graph showing representative tumor xenografts at week 6.

FIG. 7A: Graphs showing miR-21 expression analyzed by real time PCR in anti-miR-21 transfected cells compared to controls.

FIG. 7B: Graphs showing protein expression was measured by densitometric analysis.

FIG. 7C: Graph showing real time PCR analysis of hMSH2 and hMSH6 mRNA expression. Bars represent mean and S.D. of 3 experiments. *$P<0.05$.

BRIEF DESCRIPTION OF THE SEQUENCE LISTING

Figure 1A:
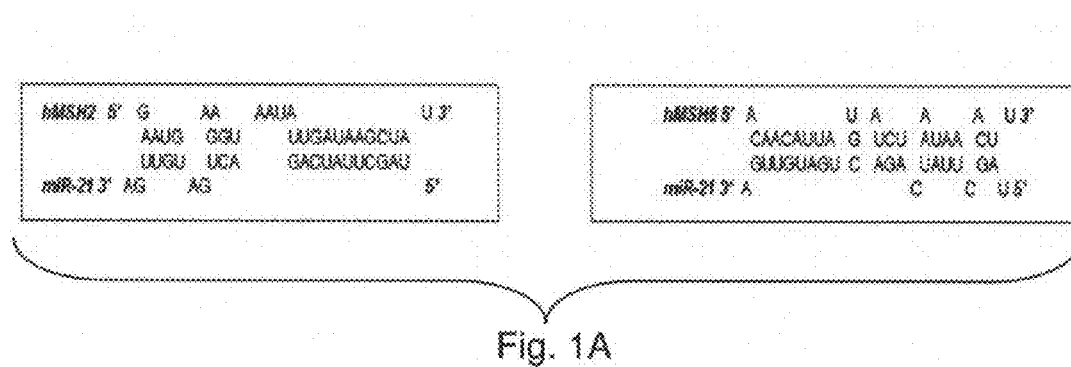
FIGS. 1A-1F. MSH2 and MSH6 are direct targets of miR-21.

The instant application contains a Sequence Listing which has been submitted via EFS-web and is hereby incorporated by reference in its entirety. The ASCII copy, created on Nov. 7, 2011, is named 53-52535_SEQ_LIST_OSURF 11085.txt, and is 3,139 bytes in size.

| Primers Name | Primer Fw 5'-3' | Primer Rv 5'-3' |
|---|---|---|
| SEQ ID NOS 1 and 6 hMSH2-LUC-WT | CAGAAAGCC CTGGAACTT GA | TCAATTGCA AACAGTCCT CAG |
| SEQ ID NOS 2 and 7 hMSH2-LUC-MUTANT | TTTCCATAG TGTTAACTG TCAGTGC | TCAATTGCA AACAGTCCT CAG |
| SEQ ID NOS 3 and 8 hMSH2-cDNA-Mutant | CCCAGTAAT GGAATGAAG GGTCTGTAA TAGTTTTAT ATTG | CAATATAAA ACTATTACA GACCCTTCA TTCCATTAC TGGG |
| SEQ ID NOS 4 and 9 hMSH6-LUC-WT | AAATGTTGC TGTGCGCCT A | TAGCTTTTC CTCCCCCAT TT |
| SEQ ID NOS 5 and 10 hMSH6-LUC-MUTANT | AAATGTTGC TGTGCGCCT A | CCACCTTTG TCAGAAGTC AACTC |

DETAILED DESCRIPTION OF THE INVENTION miR-21 is commonly over-expressed in a number of human tumors including colorectal cancer. In recent years a several of miR-21 tumor suppressor targets have been identified that may accelerate the progression of cancer. The inventors herein found an inverse relationship between colorectal tumor cells that over-express miR-21 and those that express the hMSH2 tumor suppressor protein. Moreover, the inventors determined that miR-21 appears to directly target the 3'-UTR of both the hMSH2 and hMSH6 mRNA resulting in significant down-regulation of protein expression.

The state of the art therapeutic treatment of colorectal cancer includes 5-fluorouracil (5-FU). 5-FU exerts its cytotoxic effects by misincorporation of fluoronucleotides into RNA and DNA as well as inhibiting nucleotide synthesis by targeting the thymidylate synthetase (TS) enzyme. TS overexpression, defects in 5-FU metabolism, TP53 mutations and impairment of the MMR system are all hallmarks of 5-FU resistance and predictors of clinical outcome. More recently, both microRNA and gene expression analysis have revealed a higher level of complexity in predicting 5-FU benefit in stage II and III CRC patients who underwent adjuvant chemotherapy. Indeed, a retrospective analysis of stage II and III CRC patients treated with 5-FU analogs showed reduced survival in patients with high miR-21 expression. The same findings where confirmed in the subgroup of stage III CRC patients alone, while stage II CRC patients showed no statistically significant correlation. The low number of patients may account for this latter result. Cells with genetic or epigenetic defects of the MMR machinery appear to tolerate 5-FU metabolites as a result of defects in G2/M arrest and apoptosis.

The present invention show shows that down-regulation of hMSH2 by miR-21 induces resistance to 5-FU both in a cellular model and a xenograft tumor model. Taken together, the present results show that miR-21 tumor status is likely to be an important indicator of 5-FU therapeutic efficacy.

miR-21 appears to regulate a number of cell cycle and tumor suppressor genes. The present invention also shows that down-regulation of hMSH2 plays a central role in the development of 5-FU resistance. Indeed, inhibition of 5-FU-induced apoptosis and G2/M arrest by miR-21 was comparable to that caused by siRNA-mediated selective inhibition of hMSH2. Moreover, transfection of Lovo (MSH2−) cells with miR-21 did not alter cell cycle arrest or apoptosis, demonstrating that miR-21 induced effects are dependent upon hMSH2 expression. Taken together, the present results show that inhibition of miR-21 represents a synergic treatment to overcome 5-FU resistance.

The present invention also shows that miR-21 dependent down-regulation of hMSH2-hMSH6 is responsible for both primary and acquired resistance to 5-FU. In clinical practice, 5-FU is usually administered as a continuous infusion over a 48 hours period. Interestingly, miR-21 expression appears to increase in cell lines continuously exposed to 5-FU. In light of the present invention, the inventors contend that this over-expression may be a secondary mechanism of resistance and that cells acquire miR-21 over-expression to overcome 5-FU cytotoxicity. There is additional clinical relevance if one considers that hMSH2 is frequently down-regulated after primary chemotherapy including 5-FU or Cisplatin in rectal and ovarian cancers.

In summary, the inventors have shown 5-FU drug resistance in colorectal tumors due to the over-expression of miR-21 directly down-regulates the core MMR proteins hMSH2 and hMSH6, ultimately leading to a defect in damage-induced G2/M arrest and apoptosis.

DEFINITIONS AND ABBREVIATIONS

DNA Deoxyribonucleic acid
mRNA Messenger RNA
PCR Polymerase chain reaction
pre-miRNA Precursor microRNA
qRT-PCR Quantitative reverse transcriptase polymerase chain reaction
RNA Ribonucleic acid It is to be understood that both the foregoing general description and the following detailed description are exemplary and explanatory only and are not intended to limit the scope of the current teachings. In this application, the use of the singular includes the plural unless specifically stated otherwise.

Unless otherwise noted, technical terms are used according to conventional usage. Definitions of common terms in molecular biology may be found in Benjamin Lewin, Genes V, published by Oxford University Press, 1994 (ISBN 0-19-854287-9); Kendrew et al. (eds.), The Encyclopedia of Molecular Biology, published by Blackwell Science Ltd., 1994 (ISBN 0-632-02182-9); and Robert A. Meyers (ed.), Molecular Biology and Biotechnology: a Comprehensive Desk Reference, published by VCH Publishers, Inc., 1995 (ISBN 1-56081-569-8).

In order to facilitate review of the various embodiments of the disclosure, the following explanations of specific terms are provided:

Adjunctive therapy: A treatment used in combination with a primary treatment to improve the effects of the primary treatment.

Clinical outcome: Refers to the health status of a patient following treatment for a disease or disorder or in the absence of treatment. Clinical outcomes include, but are not limited to, an increase in the length of time until death, a decrease in the length of time until death, an increase in the chance of survival, an increase in the risk of death, survival, disease-free survival, chronic disease, metastasis, advanced or aggressive disease, disease recurrence, death, and favorable or poor response to therapy.

Decrease in survival: As used herein, "decrease in survival" refers to a decrease in the length of time before death of a patient, or an increase in the risk of death for the patient.

Detecting level of expression: For example, "detecting the level of miR or miRNA expression" refers to quantifying the amount of miR or miRNA present in a sample. Detecting expression of the specific miR, or any microRNA, can be achieved using any method known in the art or described herein, such as by qRT-PCR. Detecting expression of miR includes detecting expression of either a mature form of miRNA or a precursor form that is correlated with miRNA expression. Typically, miRNA detection methods involve sequence specific detection, such as by RT-PCR. miR-specific primers and probes can be designed using the precursor and mature miR nucleic acid sequences, which are known in the art and provided herein as in the SEQ ID NOs.

MicroRNA (miRNA): Single-stranded RNA molecules that regulate gene expression. MicroRNAs are generally 21-23 nucleotides in length. MicroRNAs are processed from primary transcripts known as pri-miRNA to short stem-loop structures called precursor (pre)-miRNA and finally to functional, mature microRNA. Mature microRNA molecules are partially-complementary to one or more messenger RNA molecules, and their primary function is to down-regulate gene expression. MicroRNAs regulate gene expression through the RNAi pathway.

miR expression: As used herein, "low miR expression" and "high miR expression" are relative terms that refer to the level of miRNAs found in a sample. In some embodiments, low and high miR expression is determined by comparison of miRNA levels in a group of control samples and test samples. Low and high expression can then be assigned to each sample based on whether the expression of mi in a sample is above (high) or below (low) the average or median miR expression level. For individual samples, high or low miR expression can be determined by comparison of the sample to a control or reference sample known to have high or low expression, or by comparison to a standard value. Low and high miR expression can include expression of either the precursor or mature forms of miRNA, or both.

Patient: As used herein, the term "patient" includes human and non-human animals. The preferred patient for treatment is a human. "Patient" and "subject" are used interchangeably herein.

Pharmaceutically acceptable vehicles: The pharmaceutically acceptable carriers (vehicles) useful in this disclosure are conventional. Remington's Pharmaceutical Sciences, by E. W. Martin, Mack Publishing Co., Easton, Pa., 15th Edition (1975), describes compositions and formulations suitable for pharmaceutical delivery of one or more therapeutic compounds, molecules or agents.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Preventing, treating or ameliorating a disease: "Preventing" a disease refers to inhibiting the full development of a disease. "Treating" refers to a therapeutic intervention that ameliorates a sign or symptom of a disease or pathological condition after it has begun to develop. "Ameliorating" refers to the reduction in the number or severity of signs or symptoms of a disease.

Screening: As used herein, "screening" refers to the process used to evaluate and identify candidate agents that affect such disease. Expression of a microRNA can be quantified using any one of a number of techniques known in the art and described herein, such as by microarray analysis or by qRT-PCR.

Small molecule: A molecule, typically with a molecular weight less than about 1000 Daltons, or in some embodiments, less than about 500 Daltons, wherein the molecule is capable of modulating, to some measurable extent, an activity of a target molecule.

Therapeutic: A generic term that includes both diagnosis and treatment.

Therapeutic agent: A chemical compound, small molecule, or other composition, such as an antisense compound, antibody, protease inhibitor, hormone, chemokine or cytokine, capable of inducing a desired therapeutic or prophylactic effect when properly administered to a subject.

As used herein, a "candidate agent" or "test compound" is a compound selected for screening to determine if it can function as a therapeutic agent. "Incubating" includes a sufficient amount of time for an agent to interact with a cell or tissue. "Contacting" includes incubating an agent in solid or in liquid form with a cell or tissue. "Treating" a cell or tissue with an agent includes contacting or incubating the agent with the cell or tissue.

Therapeutically-effective amount: A quantity of a specified pharmaceutical or therapeutic agent sufficient to achieve a desired effect in a subject, or in a cell, being treated with the agent. The effective amount of the agent will be dependent on several factors, including, but not limited to the subject or cells being treated, and the manner of administration of the therapeutic composition.

In some embodiments of the present methods, use of a control is desirable. In that regard, the control may be a non-cancerous tissue sample obtained from the same patient, or a tissue sample obtained from a healthy subject, such as a healthy tissue donor. In another example, the control is a standard calculated from historical values. Tumor samples and non-cancerous tissue samples can be obtained according to any method known in the art. For example, tumor and non-cancerous samples can be obtained from cancer patients that have undergone resection, or they can be obtained by extraction using a hypodermic needle, by microdissection, or by laser capture. Control (non-cancerous) samples can be obtained, for example, from a cadaveric donor or from a healthy donor.

In some embodiments, screening comprises contacting the candidate agents/test compounds with cells. The cells can be primary cells obtained from a patient, or the cells can be immortalized or transformed cells.

The candidate agent/test compounds can be any type of agent, such as a protein, peptide, small molecule, antibody or nucleic acid. In some embodiments, the candidate agent is a cytokine. In some embodiments, the candidate agent is a small molecule. Screening includes both high-throughout screening and screening individual or small groups of candidate agents.

MicroRNA Detection

In some methods herein, it is desirable to identify miRNAs present in a sample.

The sequences of precursor microRNAs (pre-miRNAs) and mature miRNAs are publicly available, such as through the miRBase database, available online by the Sanger Institute (see Griffiths-Jones et al., Nucleic Acids Res. 36:D154-D158, 2008; Griffiths-Jones et al., Nucleic Acids Res. 34:D140-D144, 2006; and Griffiths-Jones, Nucleic Acids Res. 32:D109-D111, 2004). The sequences of the precursor and mature forms of the presently disclosed preferred family members are provided herein.

Detection and quantification of RNA expression can be achieved by any one of a number of methods well known in the art (see, for example, U.S. Patent Application Publication Nos. 2006/0211000 and 2007/0299030, herein incorporated by reference) and described below. Using the known sequences for RNA family members, specific probes and primers can be designed for use in the detection methods described below as appropriate.

In some cases, the RNA detection method requires isolation of nucleic acid from a sample, such as a cell or tissue sample. Nucleic acids, including RNA and specifically miRNA, can be isolated using any suitable technique known in the art. For example, phenol-based extraction is a common method for isolation of RNA. Phenol-based reagents contain a combination of denaturants and RNase inhibitors for cell and tissue disruption and subsequent separation of RNA from contaminants. Phenol-based isolation procedures can recover RNA species in the 10-200-nucleotide range (e.g., precursor and mature miRNAs, 5S and 5.8S ribosomal RNA (rRNA), and U1 small nuclear RNA (snRNA)). In addition, extraction procedures such as those using TRIZOL™ or TRI REAGENT™, will purify all RNAs, large and small, and are efficient methods for isolating total RNA from biological samples that contain miRNAs and small interfering RNAs (siRNAs).

In some embodiments, use of a microarray is desirable. A microarray is a microscopic, ordered array of nucleic acids, proteins, small molecules, cells or other substances that enables parallel analysis of complex biochemical samples. A DNA microarray consists of different nucleic acid probes, known as capture probes that are chemically attached to a solid substrate, which can be a microchip, a glass slide or a microsphere-sized bead. Microarrays can be used, for example, to measure the expression levels of large numbers of messenger RNAs (mRNAs) and/or miRNAs simultaneously.

Microarrays can be fabricated using a variety of technologies, including printing with fine-pointed pins onto glass slides, photolithography using pre-made masks, photolithography using dynamic micromirror devices, ink-jet printing, or electrochemistry on microelectrode arrays.

Microarray analysis of miRNAs, for example (although these procedures can be used in modified form for any RNA analysis) can be accomplished according to any method known in the art (see, for example, PCT Publication No. WO 2008/054828; Ye et al., Nat. Med. 9(4):416-423, 2003; Calin et al., N. Engl. J. Med. 353(17):1793-1801, 2005, each of which is herein incorporated by reference). In one example, RNA is extracted from a cell or tissue sample, the small RNAs (18-26-nucleotide RNAs) are size-selected from total RNA using denaturing polyacrylamide gel electrophoresis. Oligonucleotide linkers are attached to the 5' and 3' ends of the small RNAs and the resulting ligation products are used as templates for an RT-PCR reaction with 10 cycles of amplification. The sense strand PCR primer has a fluorophore attached to its 5' end, thereby fluorescently labeling the sense strand of the PCR product. The PCR product is denatured and then hybridized to the microarray. A PCR product, referred to as the target nucleic acid that is complementary to the corresponding miRNA capture probe sequence on the array will hybridize, via base pairing, to the spot at which the capture probes are affixed. The spot will then fluoresce when excited using a microarray laser scanner. The fluorescence intensity of each spot is then evaluated in terms of the number of copies of a particular miRNA, using a number of positive and negative controls and array data normalization methods, which will result in assessment of the level of expression of a particular miRNA.

In an alternative method, total RNA containing the small RNA fraction (including the miRNA) extracted from a cell or tissue sample is used directly without size-selection of small RNAs, and 3' end labeled using T4 RNA ligase and either a fluorescently-labeled short RNA linker. The RNA samples are labeled by incubation at 30° C. for 2 hours followed by heat inactivation of the T4 RNA ligase at 80° C. for 5 minutes. The fluorophore-labeled miRNAs complementary to the corresponding miRNA capture probe sequences on the array will hybridize, via base pairing, to the spot at which the capture probes are affixed. The microarray scanning and data processing is carried out as described above.

There are several types of microarrays than be employed, including spotted oligonucleotide microarrays, pre-fabricated oligonucleotide microarrays and spotted long oligonucleotide arrays. In spotted oligonucleotide microarrays, the capture probes are oligonucleotides complementary to miRNA sequences. This type of array is typically hybridized with amplified PCR products of size-selected small RNAs from two samples to be compared (such as non-cancerous tissue and cancerous or sample tissue) that are labeled with two different fluorophores. Alternatively, total RNA containing the small RNA fraction (including the miRNAs) is extracted from the two samples and used directly without size-selection of small RNAs, and 3' end labeled using T4 RNA ligase and short RNA linkers labeled with two different fluorophores. The samples can be mixed and hybridized to one single microarray that is then scanned, allowing the visualization of up-regulated and down-regulated miRNA genes in one assay.

In pre-fabricated oligonucleotide microarrays or single-channel microarrays, the probes are designed to match the sequences of known or predicted miRNAs. There are commercially available designs that cover complete genomes (for example, from Affymetrix or Agilent). These microarrays give estimations of the absolute value of gene expression and therefore the comparison of two conditions requires the use of two separate microarrays.

Spotted long oligonucleotide arrays are composed of 50 to 70-mer oligonucleotide capture probes, and are produced by either ink-jet or robotic printing. Short Oligonucleotide Arrays are composed of 20-25-mer oligonucleotide probes, and are produced by photolithographic synthesis (Affymetrix) or by robotic printing.

In some embodiments, use of quantitative RT-PCR is desirable. Quantitative RT-PCR (qRT-PCR) is a modification of polymerase chain reaction used to rapidly measure the quantity of a product of polymerase chain reaction. qRT-PCR is commonly used for the purpose of determining whether a genetic sequence, such as a miR, is present in a sample, and if it is present, the number of copies in the sample. Any method of PCR that can determine the expression of a nucleic acid molecule, including a miRNA, falls within the scope of the present disclosure. There are several variations of the qRT-PCR method known in the art, three of which are described below.

Methods for quantitative polymerase chain reaction include, but are not limited to, via agarose gel electrophoresis, the use of SYBR Green (a double stranded DNA dye), and the use of a fluorescent reporter probe. The latter two can be analyzed in real-time.

With agarose gel electrophoresis, the unknown sample and a known sample are prepared with a known concentration of a similarly sized section of target DNA for amplification. Both reactions are run for the same length of time in identical conditions (preferably using the same primers, or at least primers of similar annealing temperatures). Agarose gel electrophoresis is used to separate the products of the reaction from their original DNA and spare primers. The relative quantities of the known and unknown samples are measured to determine the quantity of the unknown.

The use of SYBR Green dye is more accurate than the agarose gel method, and can give results in real time. A DNA binding dye binds all newly synthesized double stranded DNA and an increase in fluorescence intensity is measured, thus allowing initial concentrations to be determined. However, SYBR Green will label all double-stranded DNA, including any unexpected PCR products as well as primer dimers, leading to potential complications and artifacts. The reaction is prepared as usual, with the addition of fluorescent double-stranded DNA dye. The reaction is run, and the levels of fluorescence are monitored (the dye only fluoresces when bound to the double-stranded DNA). With reference to a standard sample or a standard curve, the double-stranded DNA concentration in the PCR can be determined.

The fluorescent reporter probe method uses a sequence-specific nucleic acid based probe so as to only quantify the probe sequence and not all double stranded DNA. It is commonly carried out with DNA based probes with a fluorescent reporter and a quencher held in adjacent positions (so-called dual-labeled probes). The close proximity of the reporter to the quencher prevents its fluorescence; it is only on the breakdown of the probe that the fluorescence is detected. This process depends on the 5' to 3' exonuclease activity of the polymerase involved.

The real-time quantitative PCR reaction is prepared with the addition of the dual-labeled probe. On denaturation of the double-stranded DNA template, the probe is able to bind to its complementary sequence in the region of interest of the template DNA. When the PCR reaction mixture is heated to activate the polymerase, the polymerase starts synthesizing the complementary strand to the primed single stranded template DNA. As the polymerization continues, it reaches the probe bound to its complementary sequence, which is then hydrolyzed due to the 5'-3' exonuclease activity of the polymerase, thereby separating the fluorescent reporter and the quencher molecules. This results in an increase in fluorescence, which is detected. During thermal cycling of the real-time PCR reaction, the increase in fluorescence, as released from the hydrolyzed dual-labeled probe in each PCR cycle is monitored, which allows accurate determination of the final, and so initial, quantities of DNA.

In some embodiments, use of in situ hybridization is desirable. In situ hybridization (ISH) applies and extrapolates the technology of nucleic acid hybridization to the single cell level, and, in combination with the art of cytochemistry, immunocytochemistry and immunohistochemistry, permits the maintenance of morphology and the identification of cellular markers to be maintained and identified, and allows the localization of sequences to specific cells within populations, such as tissues and blood samples. ISH is a type of hybridization that uses a complementary nucleic acid to localize one or more specific nucleic acid sequences in a portion or section of tissue (in situ), or, if the tissue is small enough, in the entire tissue (whole mount ISH). RNA ISH can be used to assay expression patterns in a tissue, such as the expression of miRNAs.

Sample cells or tissues are treated to increase their permeability to allow a probe, such as a miRNA-specific probe, to enter the cells. The probe is added to the treated cells, allowed to hybridize at pertinent temperature, and excess probe is washed away. A complementary probe is labeled with a radioactive, fluorescent or antigenic tag, so that the probe's location and quantity in the tissue can be determined using autoradiography, fluorescence microscopy or immunoassay. The sample may be any sample as herein described, such as a non-cancerous or cancerous tissue sample. Since the sequences of miR-155 family members are known, miR-155 probes can be designed accordingly such that the probes specifically bind miR-155.

In some embodiments, use of in situ PCR is desirable. In situ PCR is the PCR based amplification of the target nucleic acid sequences prior to ISH. For detection of RNA, an intracellular reverse transcription step is introduced to generate complementary DNA from RNA templates prior to in situ PCR. This enables detection of low copy RNA sequences.

Prior to in situ PCR, cells or tissue samples are fixed and permeabilized to preserve morphology and permit access of the PCR reagents to the intracellular sequences to be amplified. PCR amplification of target sequences is next performed either in intact cells held in suspension or directly in cytocentrifuge preparations or tissue sections on glass slides. In the former approach, fixed cells suspended in the PCR reaction mixture are thermally cycled using conventional thermal cyclers. After PCR, the cells are cytocentrifuged onto glass slides with visualization of intracellular PCR products by ISH or immunohistochemistry. In situ PCR on glass slides is performed by overlaying the samples with the PCR mixture under a coverslip which is then sealed to prevent evaporation of the reaction mixture. Thermal cycling is achieved by placing the glass slides either directly on top of the heating block of a conventional or specially designed thermal cycler or by using thermal cycling ovens.

Detection of intracellular PCR products is generally achieved by one of two different techniques, indirect in situ PCR by ISH with PCR-product specific probes, or direct in situ PCR without ISH through direct detection of labeled nucleotides (such as digoxigenin-11-dUTP, fluorescein-dUTP, 3H-CTP or biotin-16-dUTP), which have been incorporated into the PCR products during thermal cycling.

Use of differentially-expressed miRs and miRNAs as predictive markers of prognosis and for identification of therapeutic agents. It is disclosed herein that certain expression patterns of miR-155, along with status indicators are predictors of survival prognosis in certain patients. As used herein, "poor prognosis" generally refers to a decrease in survival, or in other words, an increase in risk of death or a decrease in the time until death. Poor prognosis can also refer to an increase in severity of the disease, such as an increase in spread (metastasis) of the cancer to other organs. In one embodiment, the respective markers show at least a 1.5-fold increase or decrease in expression relative to the control. In other embodiments, poor prognosis is indicated by at least a 2-fold, at least a 2.5-fold, at least a 3-fold, at least a 3.5-fold, or at least a 4-fold increase or decrease in the markers relative to the wild-type tumor control figures.

Methods of screening candidate agents to identify therapeutic agents for the treatment of disease are well known in the art. Methods of detecting expression levels of RNA and proteins are known in the art and are described herein, such as, but not limited to, microarray analysis, RT-PCR (including qRT-PCR), in situ hybridization, in situ PCR, and Northern blot analysis. In one embodiment, screening comprises a high-throughput screen. In another embodiment, candidate agents are screened individually.

The candidate agents can be any type of molecule, such as, but not limited to nucleic acid molecules, proteins, peptides, antibodies, lipids, small molecules, chemicals, cytokines, chemokines, hormones, or any other type of molecule that may alter cancer disease state(s) either directly or indirectly.

Typically, an endogenous gene, miRNA or mRNA is modulated in the cell. In particular embodiments, the nucleic acid sequence comprises at least one segment that is at least 70, 75, 80, 85, 90, 95, or 100% identical in nucleic acid sequence to one or more miRNA sequence listed in Table 1. Modulation of the expression or processing of an endogenous gene, miRNA, or mRNA can be through modulation of the processing of a mRNA, such processing including transcription, transportation and/or translation with in a cell. Modulation may also be effected by the inhibition or enhancement of miRNA activity with a cell, tissue, or organ. Such processing may effect the expression of an encoded product or the stability of the mRNA. In still other embodiments, a nucleic acid sequence can comprise a modified nucleic acid sequence. In certain aspects, one or more miRNA sequence may include or comprise a modified nucleobase or nucleic acid sequence.

It will be understood in methods of the invention that a cell or other biological matter such as an organism (including patients) can be provided an miRNA or miRNA molecule corresponding to a particular miRNA by administering to the cell or organism a nucleic acid molecule that functions as the corresponding miRNA once inside the cell. The form of the molecule provided to the cell may not be the form that acts a miRNA once inside the cell. Thus, it is contemplated that in some embodiments, biological matter is provided a synthetic miRNA or a nonsynthetic miRNA, such as one that becomes processed into a mature and active miRNA once it has access to the cell's miRNA processing machinery. In certain embodiments, it is specifically contemplated that the miRNA molecule provided to the biological matter is not a mature miRNA molecule but a nucleic acid molecule that can be processed into the mature miRNA once it is accessible to miRNA processing machinery. The term "nonsynthetic" in the context of miRNA means that the miRNA is not "synthetic," as defined herein. Furthermore, it is contemplated that in embodiments of the invention that concern the use of synthetic miRNAs, the use of corresponding nonsynthetic miRNAs is also considered an aspect of the invention, and vice versa. It will be understand that the term "providing" an agent is used to include "administering" the agent to a patient.

In certain embodiments, methods also include targeting a miRNA to modulate in a cell or organism. The term "targeting a miRNA to modulate" means a nucleic acid of the invention will be employed so as to modulate the selected miRNA. In some embodiments the modulation is achieved with a synthetic or non-synthetic miRNA that corresponds to the targeted miRNA, which effectively provides the targeted miRNA to the cell or organism (positive modulation). In other embodiments, the modulation is achieved with a miRNA inhibitor, which effectively inhibits the targeted miRNA in the cell or organism (negative modulation).

In some embodiments, the miRNA targeted to be modulated is a miRNA that affects a disease, condition, or pathway. In certain embodiments, the miRNA is targeted because a treatment can be provided by negative modulation of the targeted miRNA. In other embodiments, the miRNA is targeted because a treatment can be provided by positive modulation of the targeted miRNA.

In certain methods of the invention, there is a further step of administering the selected miRNA modulator to a cell, tissue, organ, or organism (collectively "biological matter") in need of treatment related to modulation of the targeted miRNA or in need of the physiological or biological results discussed herein (such as with respect to a particular cellular pathway or result like decrease in cell viability). Consequently, in some methods of the invention there is a step of identifying a patient in need of treatment that can be provided by the miRNA modulator(s). It is contemplated that an effective amount of a miRNA modulator can be administered in some embodiments. In particular embodiments, there is a therapeutic benefit conferred on the biological matter, where a "therapeutic benefit" refers to an improvement in the one or more conditions or symptoms associated with a disease or condition or an improvement in the prognosis, duration, or status with respect to the disease. It is contemplated that a therapeutic benefit includes, but is not limited to, a decrease in pain, a decrease in morbidity, a decrease in a symptom. For example, with respect to cancer, it is contemplated that a therapeutic benefit can be inhibition of tumor growth, prevention of metastasis, reduction in number of metastases, inhibition of cancer cell proliferation, inhibition of cancer cell proliferation, induction of cell death in cancer cells, inhibition of angiogenesis near cancer cells, induction of apoptosis of cancer cells, reduction in pain, reduction in risk of recurrence, induction of chemo- or radiosensitivity in cancer cells, prolongation of life, and/or delay of death directly or indirectly related to cancer.

Furthermore, it is contemplated that the miRNA compositions may be provided as part of a therapy to a patient, in conjunction with traditional therapies or preventative agents. Moreover, it is contemplated that any method discussed in the context of therapy may be applied as preventatively, particularly in a patient identified to be potentially in need of the therapy or at risk of the condition or disease for which a therapy is needed.

In addition, methods of the invention concern employing one or more nucleic acids corresponding to a miRNA and a therapeutic drug. The nucleic acid can enhance the effect or efficacy of the drug, reduce any side effects or toxicity, modify its bioavailability, and/or decrease the dosage or frequency needed. In certain embodiments, the therapeutic drug is a cancer therapeutic. Consequently, in some embodiments, there is a method of treating cancer in a patient comprising administering to the patient the cancer therapeutic and an effective amount of at least one miRNA molecule that improves the efficacy of the cancer therapeutic or protects non-cancer cells. Cancer therapies also include a variety of combination therapies with both chemical and radiation based treatments. Combination chemotherapies include but are not limited to, for example, bevacizumab, cisplatin (CDDP), carboplatin, EGFR inhibitors (gefitinib and cetuximab), procarbazine, mechlorethamine, cyclophosphamide, camptothecin, COX-2 inhibitors (e.g., celecoxib) ifosfamide, melphalan, chlorambucil, busulfan, nitrosurea, dactinomycin, daunorubicin, doxorubicin (adriamycin), bleomycin, plicomycin, mitomycin, etoposide (VP16), tamoxifen, raloxifene, estrogen receptor binding agents, taxol, taxotere, gemcitabien, navelbine, farnesyl-protein transferase inhibitors, transplatinum, 5-fluorthe ouracil, vincristin, vinblastin and methotrexate, or any analog or derivative variant of the foregoing.

Generally, inhibitors of miRNAs can be given to achieve the opposite effect as compared to when nucleic acid molecules corresponding to the mature miRNA are given. Similarly, nucleic acid molecules corresponding to the mature miRNA can be given to achieve the opposite effect as compared to when inhibitors of the miRNA are given. For example, miRNA molecules that increase cell proliferation can be provided to cells to increase proliferation or inhibitors of such molecules can be provided to cells to decrease cell proliferation. The present invention contemplates these embodiments in the context of the different physiological effects observed with the different miRNA molecules and miRNA inhibitors disclosed herein. These include, but are not limited to, the following physiological effects: increase and decreasing cell proliferation, increasing or decreasing apoptosis, increasing transformation, increasing or decreasing cell viability, reduce or increase viable cell number, and increase or decrease number of cells at a particular phase of the cell cycle. Methods of the invention are generally contemplated to include providing or introducing one or more different nucleic acid molecules corresponding to one or more different miRNA molecules. It is contemplated that the following, at least the following, or at most the following number of different nucleic acid molecules may be provided or introduced: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, or any range derivable therein. This also applies to the number of different miRNA molecules that can be provided or introduced into a cell.

The principle and mode of operation of this invention have been explained and illustrated in its preferred embodiment. However, it must be understood that this invention may be practiced otherwise than as specifically explained and illustrated without departing from its scope.

EXAMPLES

Example 1

Materials and Methods
Cell Cultures and Transfection

Colo-320DM, SW620, SW480, HCT-116 and RKO colorectal cancer (CRC) cells (American Type Culture Collection ATCC Manassas, Va.) were cultured in RPMI 1640 (Gibco, Carlsbad, Calif.), and packaging cells 293TN (System Biosciences, Mountain View, Calif.) were grown in DMEM (Gibco, Carlsbad, Calif.). Lovo+chr2hMSH2+/2 and Lovo(DT40.2)-4-1hMSH22/2 1 were grown in IMDM (Gibco, Carlsbad, Calif.) containing 700 mg/ml G418 (Gibco). All cells were supplemented with 10% fetal bovine serum (Sigma, St. Louis, Mo.) plus antibiotics. Cells were examined for *Mycoplasma* contamination periodically and were always found negative. Cells were transfected in 6-well plates by using Lipofectamine 2000 (Invitrogen, Carlsbad, Calif.) following manufacturer's protocol. For over-expression studies specific miRNA or control precursor oligonucleotides were purchased from Ambion (Austin, Tex.) and used at 50 nM. On-target-plus siRNA to hMSH2 and hMSH6 (Dharmacon, Colo.) were used as control. For silencing experiments miRCURY LNA™ anti-miR-21 or control miRCURY knockdown probe (Exiqon, Vedbaek, Denmark) were used at 50 nM. miRNA expression was verified after 48 hours by quantitative real time PCR as described below. Plasmids encoding the full length MSH2 cDNA were purchased from Origene. The hMSH2 mutant for the miR-21 seed region was prepared using QuikChange site-directed mutagenesis kit (Stratagene, San Diego, Calif.) (Table 2).

TABLE 2

List of primers used for cloning

| Primers Name | Primer Fw 5'-3' | Primer Rv 5'-3' |
|---|---|---|
| SEQ ID NOS 1 and 6 hMSH2-LUC-WT | CAGAAAGCC CTGGAACTT GA | TCAATTGCA AACAGTCCT CAG |
| SEQ ID NOS 2 and 7 hMSH2-LUC-MUTANT | TTTCCATAG TGTTAACTG TCAGTGC | TCAATTGCA AACAGTCCT CAG |
| SEQ ID NOS 3 and 8 hMSH2-cDNA-Mutant | CCCAGTAAT GGAATGAAG GGTCTGTAA TAGTTTTAT ATTG | CAATATAAA ACTATTACA GACCCTTCA TTCCATTAC TGGG |
| SEQ ID NOS 4 and 9 hMSH6-LUC-WT | AAATGTTGC TGTGCGCCT A | TAGCTTTTC CTCCCCCAT TT |
| SEQ ID NOS 5 and 10 hMSH6-LUC-MUTANT | AAATGTTGC TGTGCGCCT A | CCACCTTTG TCAGAAGTC AACTC |

Luciferase Assay

The predicted miRNA binding sites in the 3'-UTR of hMSH2 and hMSH6 were cloned downstream of the firefly luciferase gene as follows. Complimentary DNA (cDNA) and genomic DNA from SW-480 cells was amplified by PCR using specific primers for hMSH2 and hMSH6 cloning respectively (Table 2). The product was then digested with SpeI and SacII (New England Biolabs Ipswich, Mass.) and inserted into the pGL3 control vector (Promega, Madison, Wis.) previously modified to harbor the SpeI and SacII sites immediately downstream of the stop codon of the firefly luciferase gene. Reporter constructs with mutated miRNA recognition sequences were constructed for each single gene (MUT-21). For both hMSH2 and hMSH6 miR-21 seed regions, mutant constructs were obtained using primers sited up or downstream of the predicted miRNA binding site in order to exclude the seed-region complementary sites.

Colo-320DM and SW480 cells were co-transfected in 12-well plates with 1 μg of pGL3 firefly luciferase reporter control vector, 0.1 μg of the phRL-SV40 control vector (Promega, Madison, Wis.), and 50 nM miRNA, control precursors, LNA against miR-21 or LNA control. Firefly and Renilla luciferase activities were measured consecutively by using the Dual Luciferase Assay (Promega) 24 hours after transfection.

Western Blotting

For immunoblotting analysis cells were lysed with ice-cold Cell Lysis Buffer plus protease inhibitor (Cell Signaling Technology Inc. Danvers, Mass.). Equivalent amounts of protein were resolved and mixed with 4×SDS-PAGE sample buffer, electrophoresed in a 4%-20% and 7.5% linear gradient Tris-HCL Criterion Precast Gels (Bio-Rad), and transferred to nitrocellulose or PVDF membranes (Bio-Rad). The membranes were blocked with 5% nonfat dry milk in Tris-buffered saline, pH 7.4, containing 0.05% Tween 20, and were incubated with primary and secondary antibodies according to the manufacturer's instructions. The following primary antibodies were used: mouse monoclonal anti-MSH2 (1:200, Invitrogen), mouse monoclonal anti-MSH6 (1:500, BD Biosciences San Jose, Calif.), mouse monoclonal anti-actin (1:5000, Sigma), mouse monoclonal anti-GAPDH (1:1000, SantaCruz Biotechnology).

Real Time PCR for Mature miRNAs and Genes

Total RNA was isolated with Trizol (Invitrogen). Mature miRNAs were assessed by the single-tube TaqMan MicroRNA Assay, while the expression of mRNAs of interest evaluated by the Gene Expression Assay with the following probes: hMSH2=Hs00953523_m1, hMSH6=Hs00943001_m1 (Applied Biosystems, Foster City, Calif.). miRNA expression was normalized to that of RNU44 and RNU48. Gene expression was normalized to vinculin. All retrotranscriptase (RT) reactions, including no-template controls and RT minus controls, were run in a GeneAmp PCR 9700 Thermocycler (Applied Biosystems). Each sample was tested in triplicate unless otherwise specified.

Northern Blotting

For mature miRNA detection, acrilamide Northern blotting was performed as previously described 2.

MiRNA Locked Nucleic Acid (LNA) In Situ Hybridization of Formalin Fixed, Paraffin-Embedded Tissue Section.

MicroRNA detection was performed on colon cancer tissue array (US Biomax BC05118) containing 50 normal and cancer colon cores in duplicate by in situ hybridization (ISH) as previously described3. The negative controls included omission of the probe and the use of a scrambled LNA probe. After in situ hybridization for the miRNAs, the slides were analyzed for immunohistochemistry using the optimal conditions for hMSH2 (Ventana cat #760-4265). For immunohistochemistry, the inventors used the Ultrasensitive Universal Fast Red system from Ventana Medical Systems (Tucson, Ariz.). Pictures of representative spots have been taken with the Nuance system (Ventana). Cancer cores were scored for miR-21 and hMSH2 proteins expression based on the number of positive cells in the core.

Tissue Collection

Fresh frozen tissues from tumor and normal adjacent tissue from 83 consecutive cases of CRC were collected at the Istituto Scientifico Romagnolo per lo Studio e la Cura dei Tumori, Meldola, Italy after approval of the ethical committee. Cell lysates for protein and RNA extraction were extracted as above mentioned, Cell Cycle Analyses and Apoptosis Analysis Propidium iodide (PI) staining: cells were detached with trypsin, washed with cold phosphate-buffered saline (PBS)-5% FCS and then fixed in 70% ethanol for 24 h. After washing with PBS, cells were incubated with 1 µg/ml PI for 3 h at 25° C. before FACS analysis by Coulter Epics XL flow cytometer (Beckman Coulter, Fullerton, Calif.). Cells were considered apoptotic when their DNA content was <2N. AnnexinV staining: Cells were detached with trypsin, washed with PBS-5% FCS and then placed in binding buffer containing 0.14 M NaCl, 2.5 mM CaCl2 and 0.01 M N-2-hydroxyethylpiperazine-N'-2-ethanesulfonic acid (pH 7.4) to which 7-aminoactinomycin D (7-AAD) and annexin V-FITC (Pharmingen, San Diego, Calif.) were added prior to FACS analysis. Cells were considered apoptotic when annexin V-FITC positive and 7-AAD negative.

Synchronization experiments were run as follow: Lovo-MSH2 positive, Lovo-MSH2 negative, SW620 and Colo-320DM cells were synchronized by arrest in G0-G1 via confluence and low serum treatments for 48 hours 4, cells were then dissociated with trypsin, counted, transfected with Pre-miR-control, Pre-miR-21, siRNA agains hMSH2, siRNA-control and vectors encoding for the full length MSH2 cDNA (with or without miR-21 seed region) using Cell Nucleofector® Kit (Lonza Walkersville, Inc ME) or Lipofectamine 2000™ (Invitrogen, Carlsbad, Calif.) following manufacturer instructions and replated in medium containing 10% FBS. 5-Fluorouracil (50 ug/m15) addition occurred at 16 h after release, corresponding to a time just prior to entry into S phase but after the p53-mediated G1-S cell cycle checkpoint.

Generation of Stable Clones Over-expressing miR-21

Lovo-MSH2 positive and Lovo-MSH2 negative cells were stably infected with the pCDH-CMV-MCS-EF1-miRNA expression plasmid containing the full-length miR-21 and the GFP gene under the control of two different promoters (System Biosciences, Mountain View, Calif.). An empty vector was used as control. Pre-miR-21 expression and control constructs were packaged with pPACKH1 Lentivector Packaging Plasmid mix (System Biosciences) in 293-TN packaging cell line. Viruses were concentrated using PEG-It™ Virus Precipitation Solution and titers analyzed using UltraRapid Lentiviral Titer Kit (System Biosciences). Infected cells were selected by FACS analysis (FACS Calibur, Becton Dickinson Immunocytometry Systems). Infection efficiency >90% was verified by fluorescent microscopy and further confirmed by real time PCR for miR-21 expression.

Xenografts Studies.

Animal studies were performed according to institutional guidelines. Lovo MSH2-positive cells infected with lentiviral vectors encoding for either miR-21, siRNA to hMSH2 or empty vector as control and Lovo hMSH2-negative infected with empty virus were injected in the flank of nude mice (5×106). When xenografts (6 animals for each group) reached a palpable volume, 5-FU (50 mg/kg/day) was administered by intraperitoneal injection for 5 consecutive days a week for 2 weeks. Tumor volume was measured at the beginning of treatment and then once a week. The estimated tumor volume (V) was calculated by the following formula: $V=W2\times L\times 0.5$, where W represents the largest tumor diameter in centimeters and L represents the next largest tumor diameter. The individual relative tumor volume (RTV) was calculated as follows $RTV=Vx/V1$ where Vx is the volume in cubic millimeters at a given time and V1 is the volume at the start of treatment.

Example 2 miR-21 Directly Targets hMSH2 and hMSH6 Protein Expression

Figure 1B:
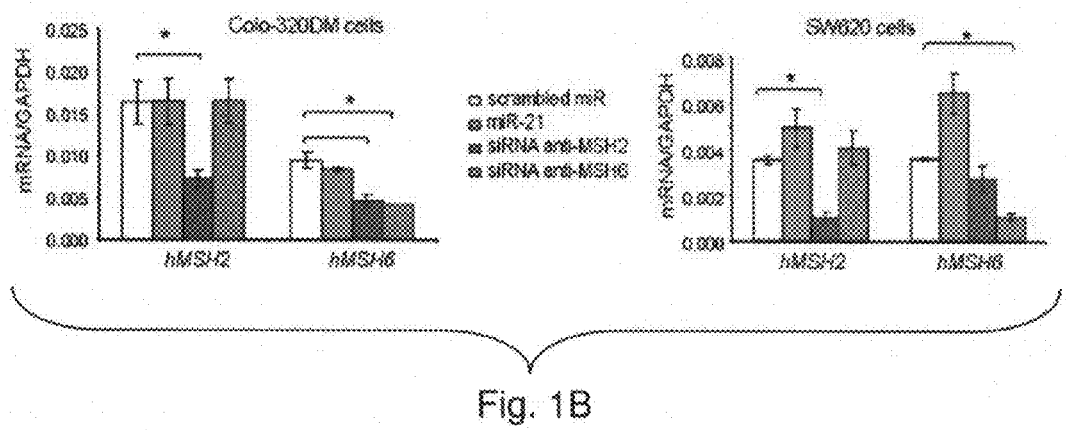
Figure 6A:
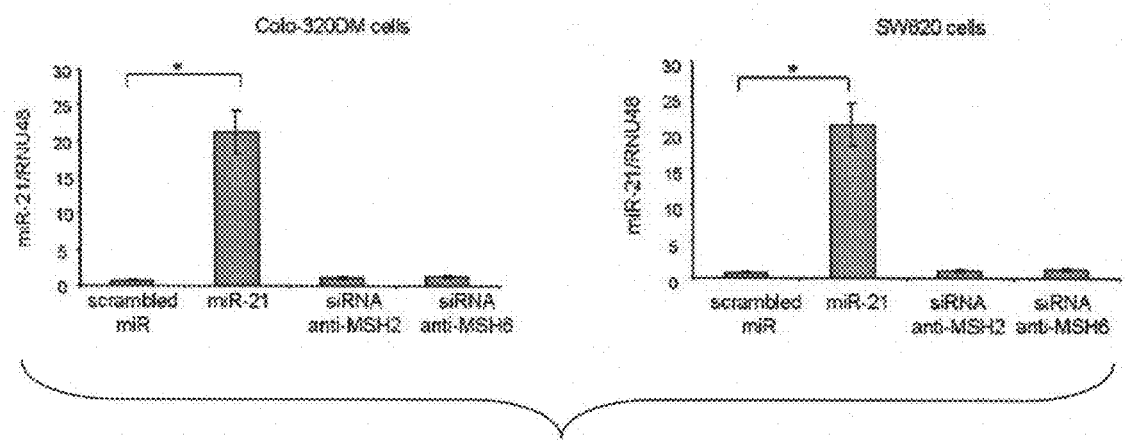
FIG. 6A: Graphs showing Colo-320DM and SW620 were transiently transfected with miR-21, scrambled-miR, siRNA anti-MSH2 or anti-MSH6 for 48 hours. miR-21 expression was assessed by real time PCR.
Figure 6B:
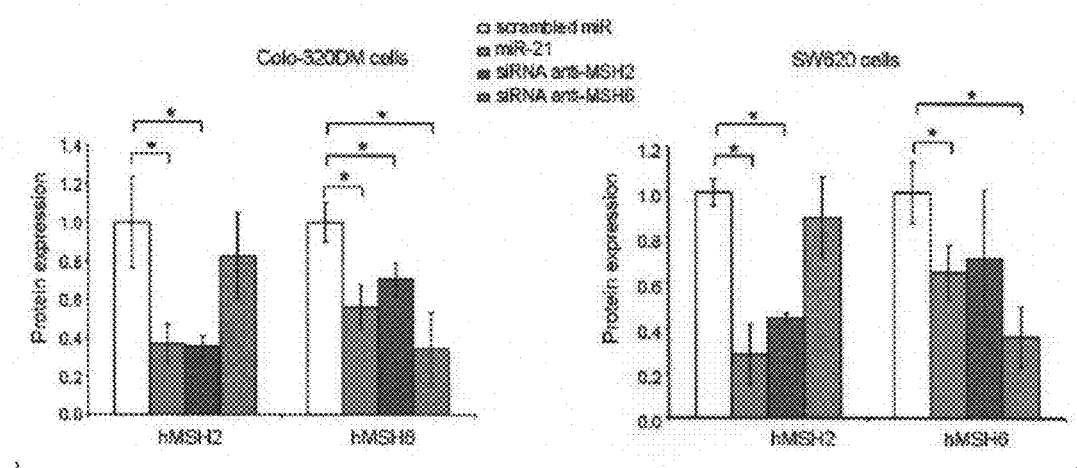
FIG. 6B: Graphs showing protein expression was measured by densitometric analysis. Bars represent mean and S.D. of 3 experiments. *$P<0.05$.

In silico analysis showed that miR-21 might target hMSH2 and hMSH6 mRNA (TargetScan, Whitehead Institute, MIT, FIG. 1A). The inventors identified a putative binding sites for miR-21 in both hMSH2 (NCBI NM_000249.2) and hMSH6 (NCBI NM_000179.2) 3'-UTR. The inventors examined the effect of miR-21 expression on endogenous hMSH2 and hMSH6 mRNA expression in CRC Colo-320DM and SW620 cells. Both cell lines display low basal miR-21 expression. The inventors transfected these cell lines with miR-21 precursor (miR-21) or a scrambled miR precursor control (FIG. 6). Over-expression of a specific small-interfering RNA (siRNA) to hMSH2 (anti-MSH2) or hMSH6 (anti-MSH6) did not affect the levels of miR-21 (FIG. 6A). The mRNA levels of hMSH2 and hMSH6 were unaffected by over-expression of miR-21 (FIG. 1B). In contrast, anti-MSH2 and anti-MSH6 siRNA specifically reduced the expression of hMSH2 and hMSH6 mRNA respectively (FIG. 1B). The inventors note a consistent reduction in the expression of hMSH6 mRNA with the anti-MSH2 siRNA. This reduction could be a result of degenerate hybridization of the anti-MSH2 siRNA with the hMSH6 mRNA or reduced hMSH6 mRNA stability resulting from the diminished heterodimeric protein partner hMSH2. The present results show that miR-21 over-expression does not affect the mRNA levels of hMSH2 or hMSH6.

Figure 1C:
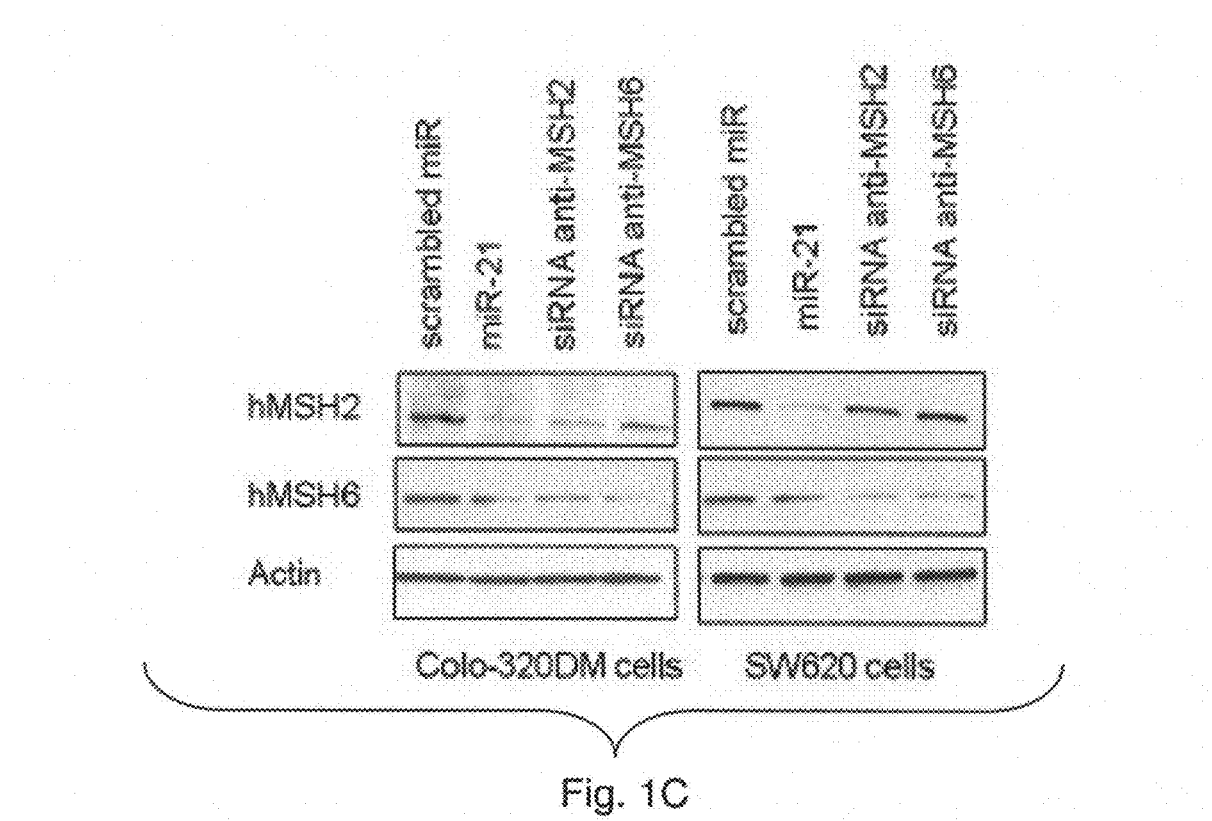
Figure 1D:
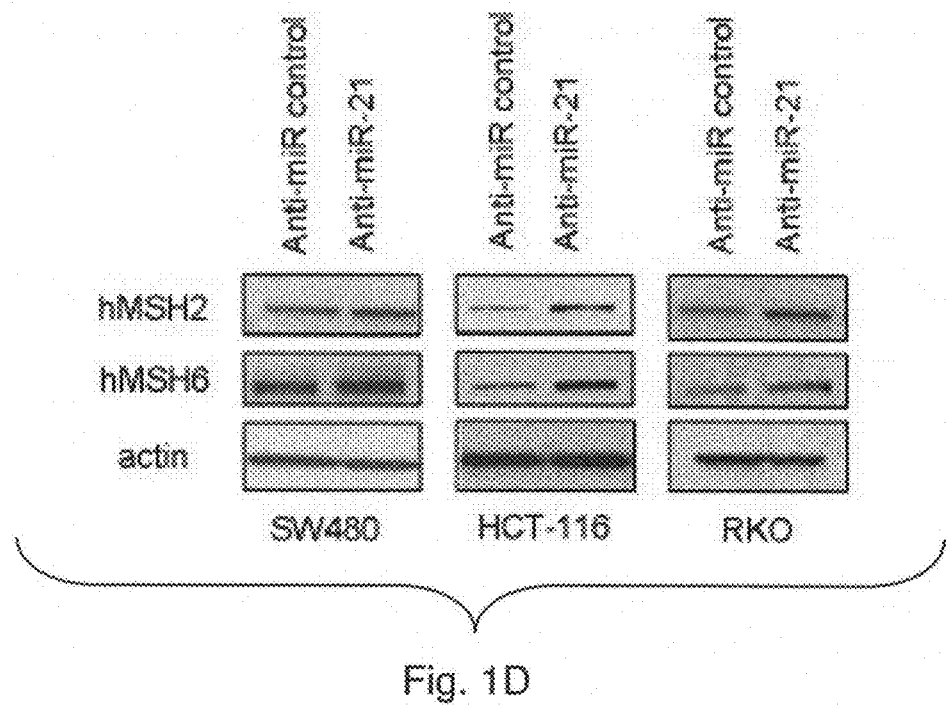
Figure 7A:
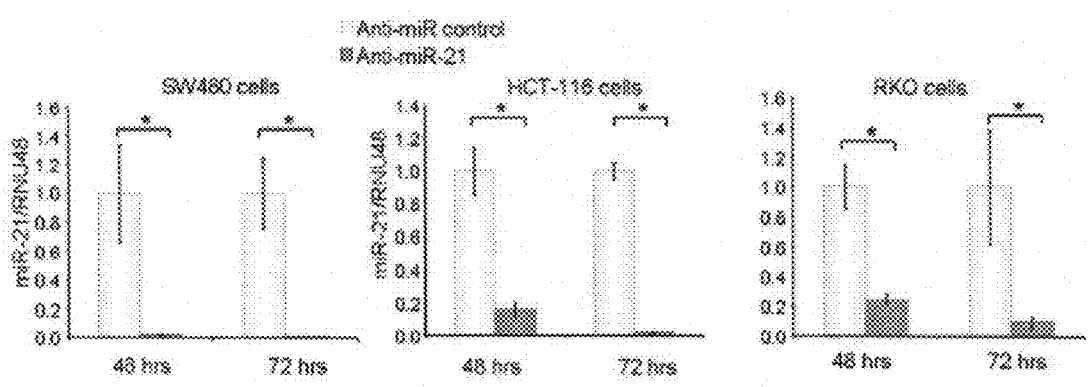
FIGS. 7A-7C: HCT-116, SW480 and RKO cells were transfected with an LNA to miR-21 (anti-miR-21) or LNA controls. 48 hours after transfection cells were harvested and RNAs and proteins were collected.
Figure 7B:
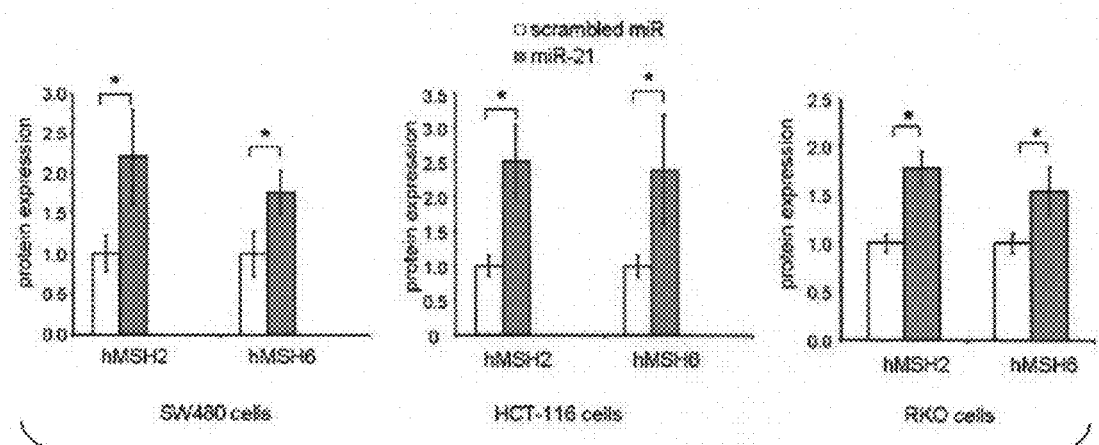
Figure 7C:
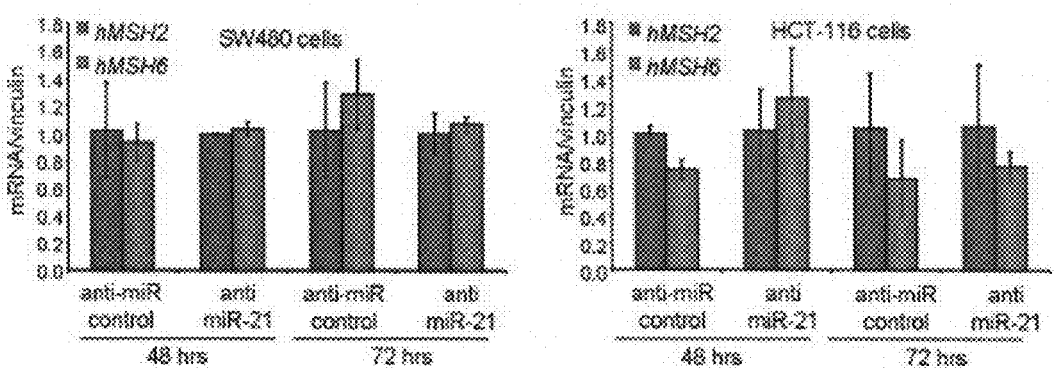

The inventors examined the protein levels of hMSH2 and hMSH6 following transfection of miR-21 in Colo-320DM and SW620 cells by western blotting analysis (FIG. 1C, FIG. 6B). hMSH2 and hMSH6 proteins were significantly reduced in cells over-expressing miR-21 compared to the scrambled miR. The anti-MSH2 and anti-MSH6 siRNA were transfected in these cell lines in parallel. The inventors observed that miR-21 transfected cells displayed a down-regulation of hMSH2 and hMSH6 that appeared comparable to cells transfected with siRNAs. Conversely, the inventors transfected CRC SW480, HCT116 and RKO cells that contain high levels of endogenous miR-21 with a locked nucleic acid (LNA) against miR-21 (anti-miR-21) or a scrambled LNA (anti-miR control). The inventors found that cells transfected with anti-miR-21 showed an increase in both hMSH2 and hMSH6 protein expression (FIG. 1D; FIG. 7B), while no changes in mRNA levels was observed (FIG. 7C).

Figure 1E:
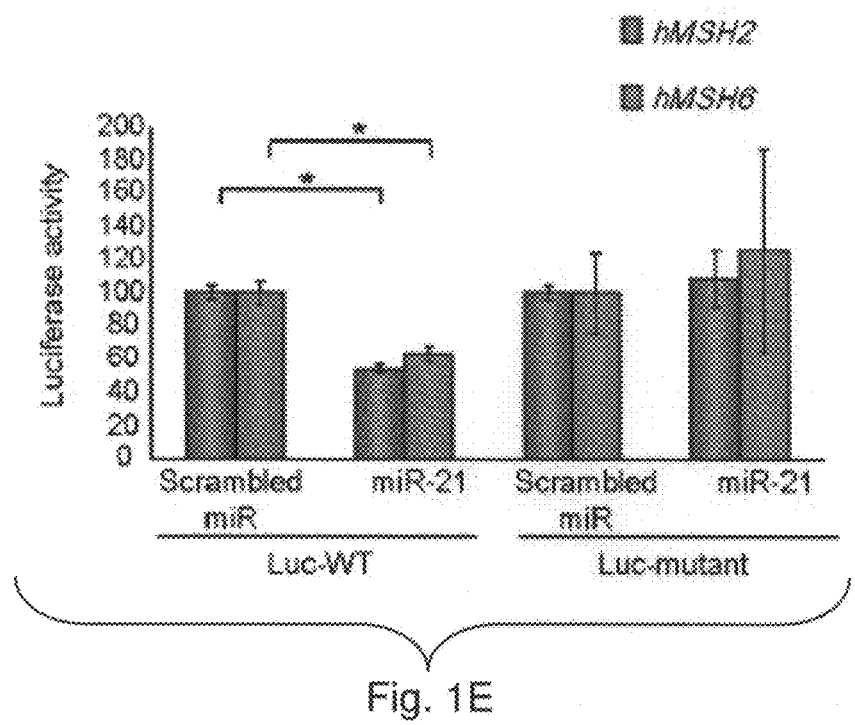
Figure 1F:
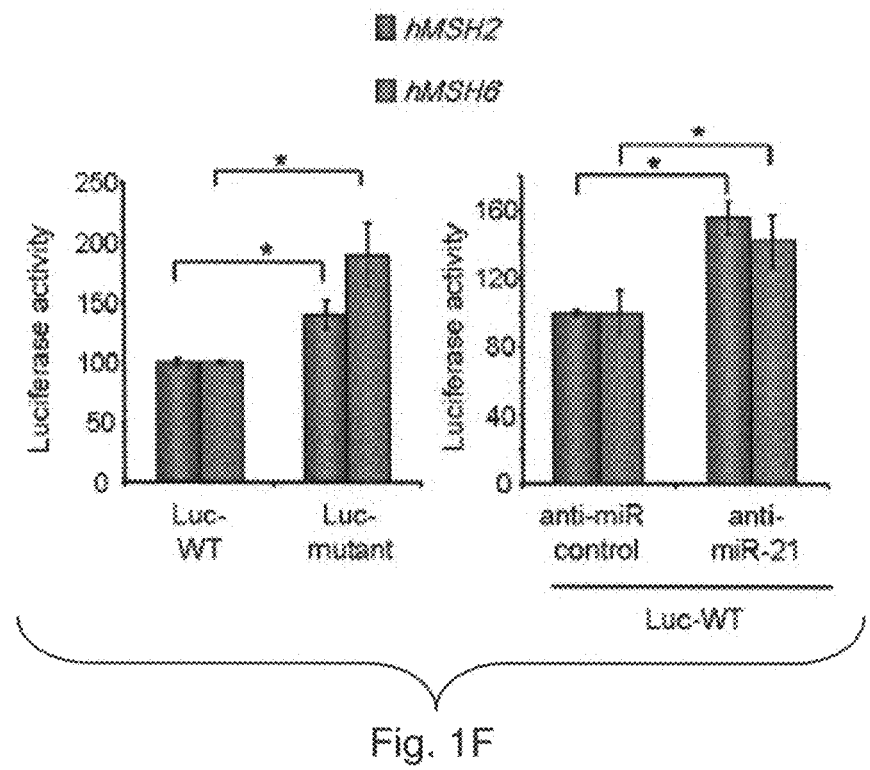

The entire 3'UTR of hMSH2 or hMSH6 was sub-cloned downstream of the luciferase gene. The luciferase reporter construct along with a precursor miR-21 (miR-21) or scrambled miR was then transfected into the Colo-320DM cells. The inventors observed a 50% and 37% reduction in the luciferase activity with constructs containing the miR-21 seed regions for hMSH2 or hMSH6 respectively (p<0.001; FIG. 1E). Deletion of the miR-21 seed regions resulted in the restoration of luciferase activity for both vectors containing hMSH2 or hMSH6 (FIG. 1E). The inventors transfected SW480 cells that displayed high levels of miR-21 expression with a luciferase reporter vector containing the wild type (WT) or mutated (mutant) hMSH2 and hMSH6 3'-UTR seed region (FIG. 1F). As expected, the inventors found that ablation of the miR-21 binding site resulted in increased luciferase activity for both the hMSH2 and hMSH6-vector transfected cells. To confirm these observations, SW480 cells were co-transfected with the hMSH2 and hMSH6 3'-UTR luciferase reporter plus the LNA anti-miR-21 or anti-miR control. LNA silencing of miR-21 induced an increase in luciferase activity (FIG. 1F). Taken as a whole, the present results show that miR-21 exerts a direct effect on the hMSH2 and hMSH6 3'-UTR that ultimately regulates hMSH2 and hMSH6 protein expression. Since hMSH2 protein status can affect hMSH6 protein stability and expression (9), the inventors cannot exclude the possibility that miR-21 regulation and hMSH2 protein loss can contribute to hMSH6 down-regulation.

Example 3 miR-21 is Inversely Correlated to the MMR Core Protein hMSH2 in CRC Tissues

Figure 2A:
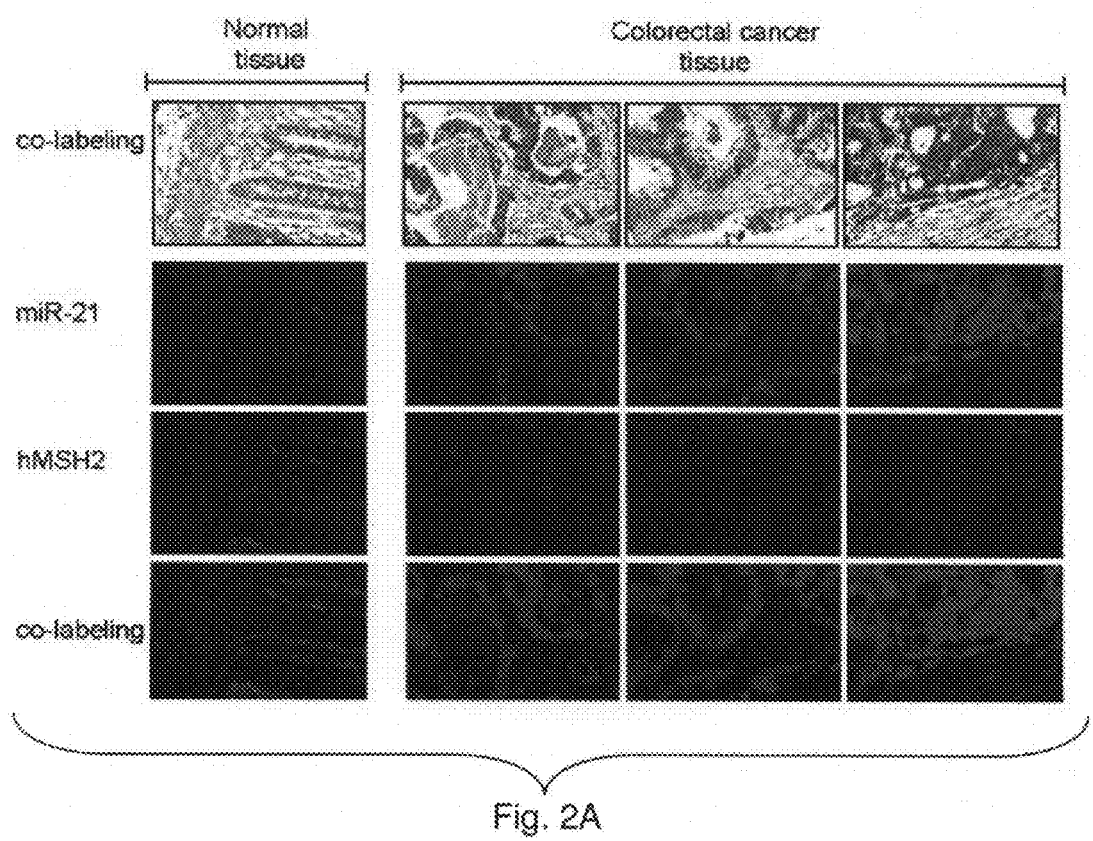
FIGS. 2A-2B. The MMR core protein hMSH2 expression is inversely correlated to mir-21 expression in CRC samples.
Figure 2B:
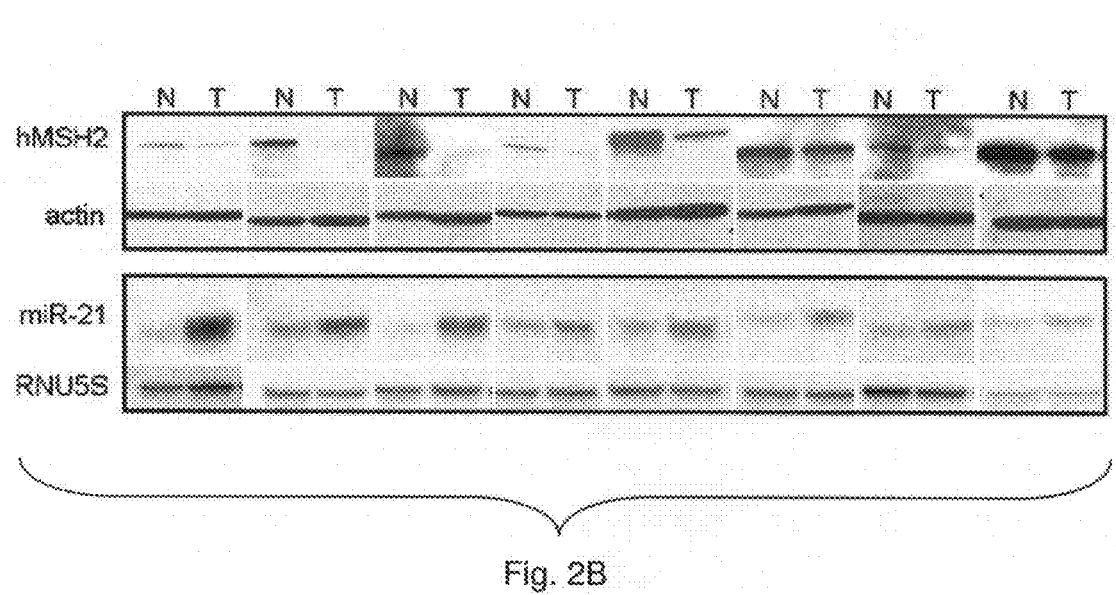

The inventors examined miR-21 and hMSH2 expression in two different CRC cohorts (FIG. 2). A tissue microarray containing 50 unselected cases of CRC and paired normal adjacent tissue was hybridized with an LNA anti-miR-21 or nonspecific LNA anti-miR control combined with immunohistochemical (IHC) staining for hMSH2 protein (FIG. 2A). A score for both miR-21 and hMSH2 protein expression was given according to the percentage of positive cell in the core. Forty-two out of fifty cores were available for matched analysis of tumor and paired normal tissue. The inventors found that miR-21 was up-regulated in 28 (66%) of these cases when tumor was compared to normal paired tissue. 14 out of 42 (33%) cases had a strong downregulation of hMSH2 in tumor compared to normal tissue. In all these cases miR-21 was found to be up-regulated. Parson correlation analysis in this sub-group of patients showed an r value of −0.82 (p<0.001). Correlation analysis on the entire cohort of cases showed an r value of −0.63. CRC tissues scored positive for both miR-21 and hMSH2 showed no co-expression in the same cancer nest (see FIG. 2A, co-labeling).

Figure 8:
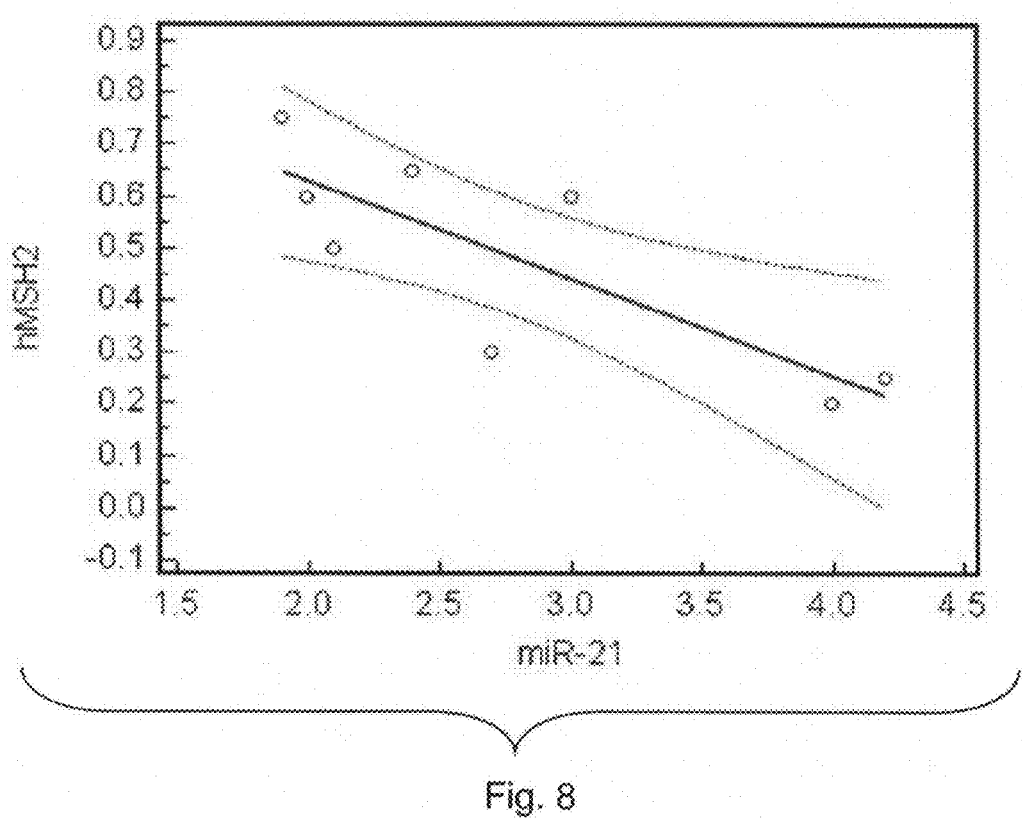
FIG. 8. Scatter plot and regression curve plus confidence interval (red) of cases displaying high miR-21 and low hMSH2 expression. miR-21 was analyzed by Northern Blotting and hMSH2 by Western Blotting analysis in tumor and normal adjacent tissue. In the graph miR-21 and hMSH2 are expressed as ratio between tumor and normal tissue. Correlation is −0.81, 95% confidence Interval: −0.96 to −0.25, $p<0.02$.

The inventors examined fresh frozen tumors from a second cohort of CRC samples for which cancer and normal adjacent tissues were available (FIG. 2B). miR-21 expression was determined by northern analysis and RT-PCR, while hMSH2 protein expression was determined by western analysis. Twenty-six cases showed hMSH2 down-regulation in tumors compared to normal adjacent tissue. miR-21 expression was found to be increased in 24 of these cases (90%) when tumor was compared to adjacent normal tissues. Since miR-155 can affect the expression of hMSH2 and other MMR proteins, the inventors excluded those cases showing simultaneous over-expression of miR-155 and miR-21 (16 cases) from this analysis. An inverse correlation (r=−0.81 p<0.02) was still evident in remaining 8 cases highlighting the inverse correlation between miR-21 over-expression and hMSH2 down-regulation in CRC tumors (FIG. 2B: FIG. 8).

Example 4 miR-21 Reduces G2/M Arrest and Apoptosis Following Exposure to 5-Fluorouracil

Figure 3A:
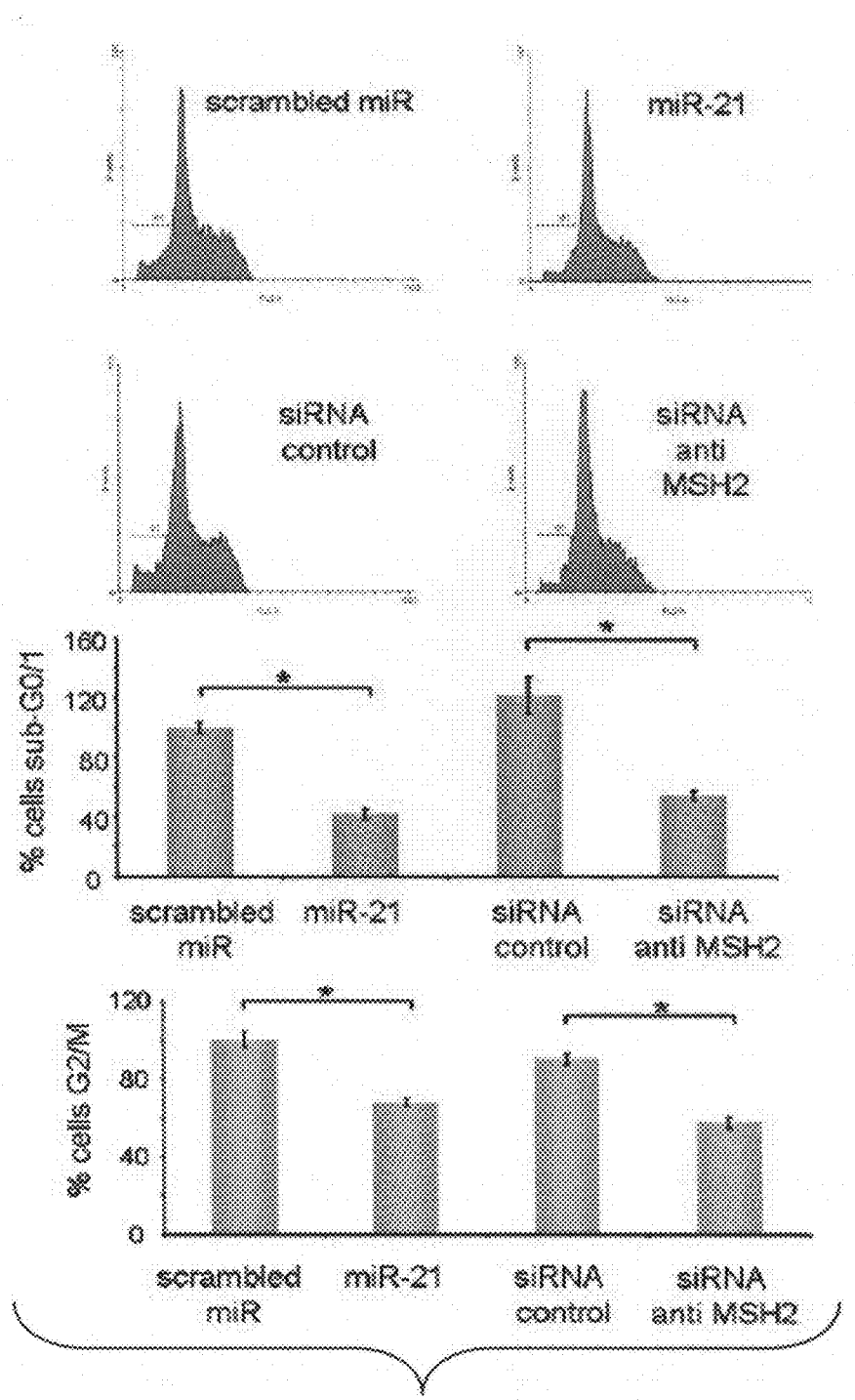
FIGS. 3A-3B. Graphs showing miR-21 inhibits 5-FU induced apoptosis in vitro. SW620 and Colo-320DM cells were synchronized at G0-G1 by serum starvation for 48 hours. Cells were then trypsinized, counted, transfected with scrambled miR, miR-21, siRNA anti-MSH2 or siRNA-control, and re-plated in medium containing 10% FBS. 5-FU was added at 16 h after release, corresponding to a time just prior to entry into S phase but after the p53-mediated G1-S cell cycle checkpoint. Cell cycle was analyzed 48 hours after 5-FU administration. Quantitation of percentage of G2/M arrested and apoptotic (sub-G1) cells are shown and represent mean and S.D. from 3 determinations from 3 independent transfections. * $p<0.001$.
Figure 3B:
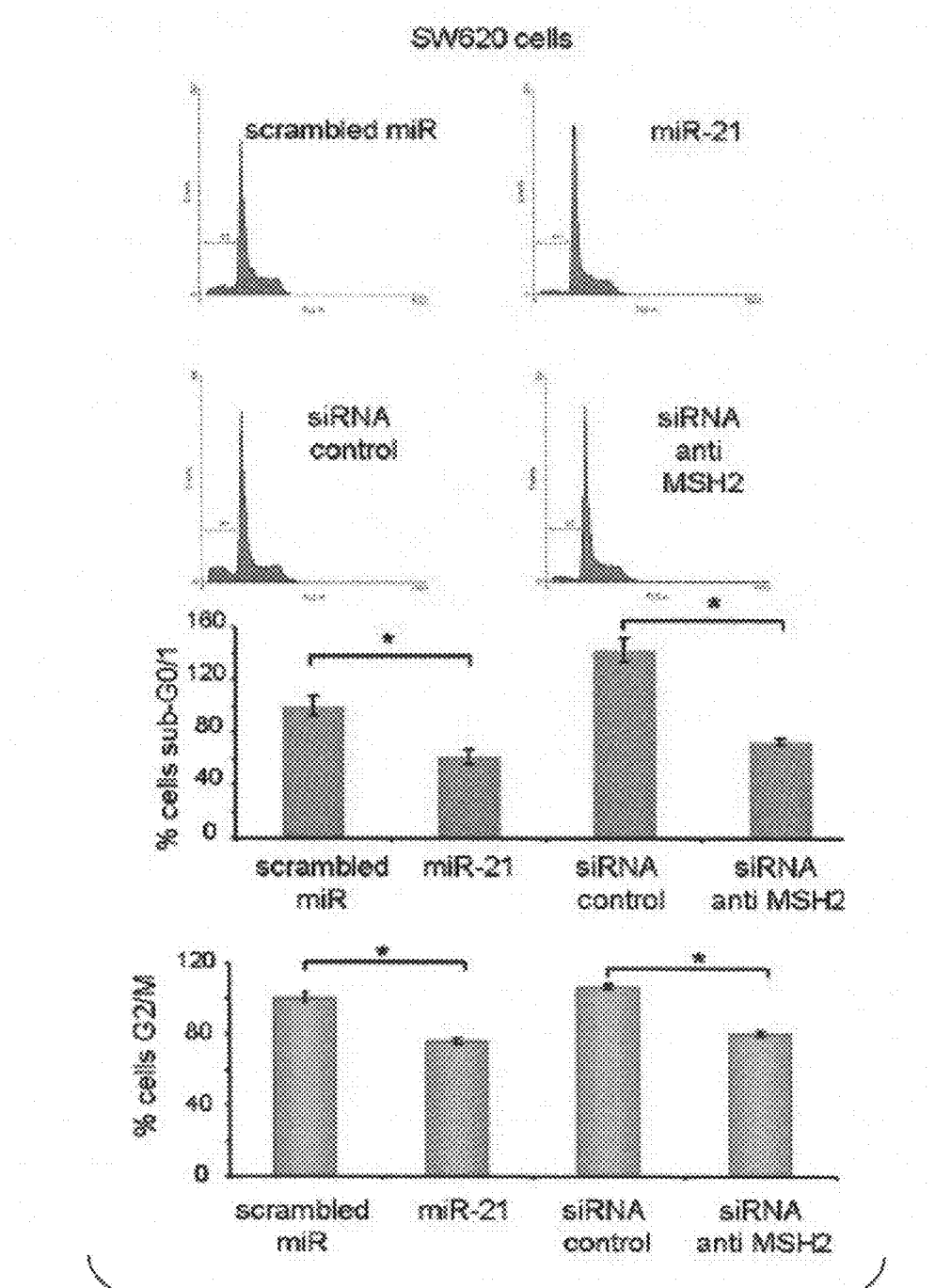
Figure 4A:
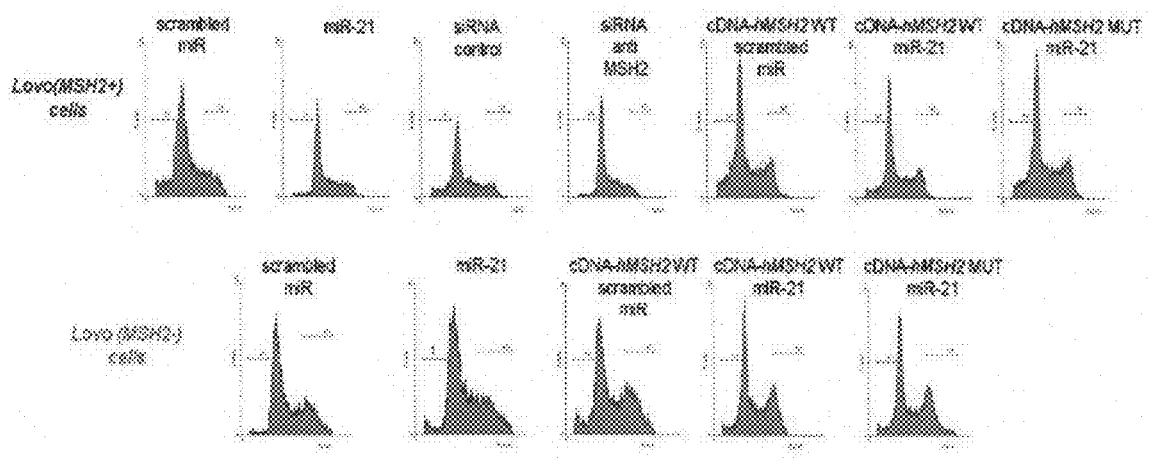
FIGS. 4A-4C. Graphs showing miR-21 mediated 5-FU resistance is dependent upon hMSH2 down-modulation. Lovo(MSH2+) and Lovo(MSH2−) cells were synchronized at G0-G1 by serum starvation for 48 hours and transfected with miR-control, miR-21, siRNA anti-MSH2, siRNA-control, along with vectors encoding the full length hMSH2 cDNA (with or without miR-21 seed region). Cell cycle was analyzed 48 hours after 5-FU administration. Quantitation of percentage of G2/M arrested and apoptotic (sub-G1) cells in both Lovo(MSH2+) cells (blue bars) and Lovo(MSH2−) cells (pink bars) are shown and represent mean and S.D. from 2 determinations from 3 independent experiments (* $p<0.001$).
Figure 4B:
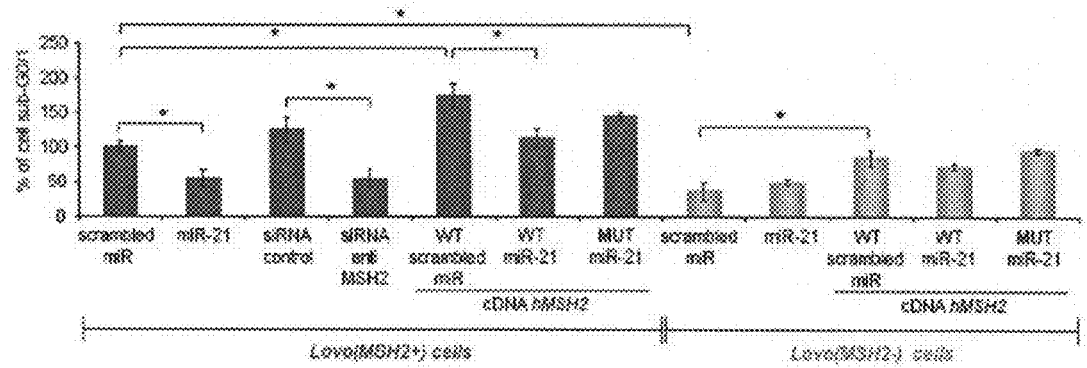
Figure 4C:
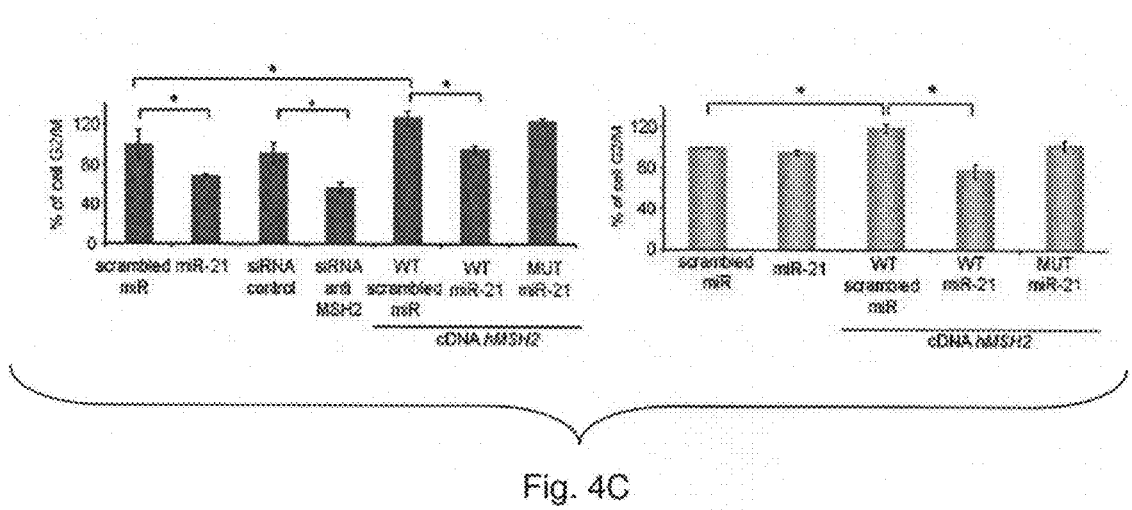
Figure 9:
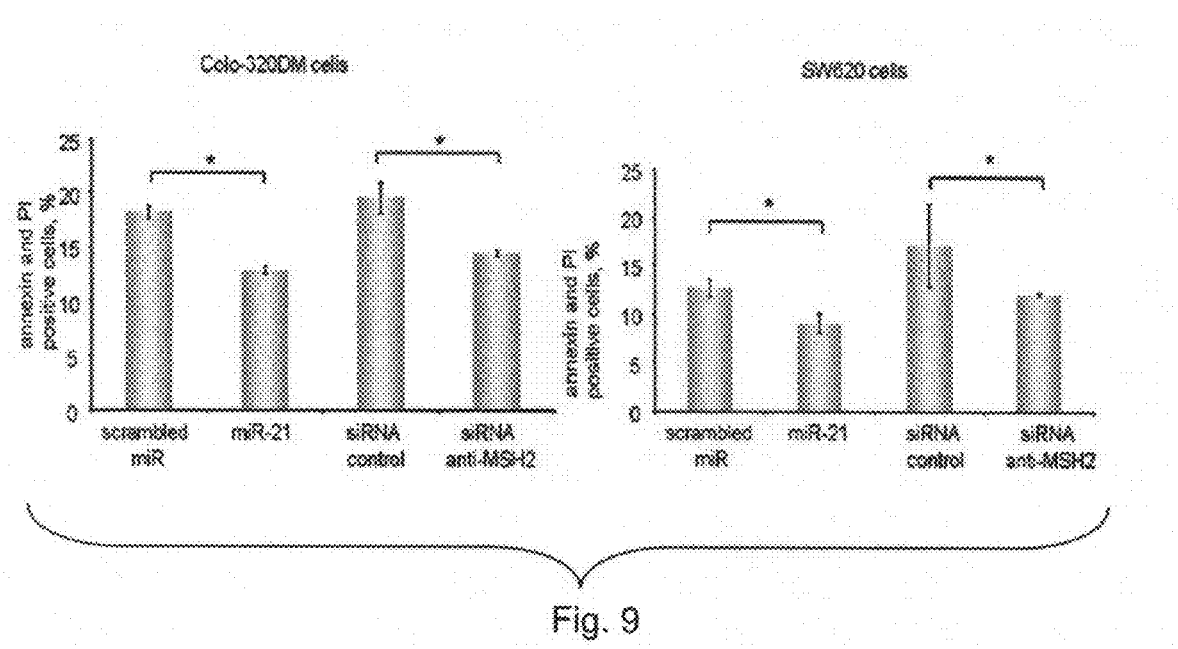
FIG. 9. SW620 and Colo-320DM cells were synchronized at G0-G1 by serum starvation for 48 hours. Cells were then trypsinized, counted, transfected with scrambled miR, miR-21, siRNA anti-MSH2 or siRNA-control, and re-plated in medium containing 10% FBS. 5-FU (50 ug/ml) was added at 16 h after release, corresponding to a time just prior to entry into S phase but after the p53-mediated G1-S cell cycle checkpoint. The percentage of apoptotic cells was analyzed by FACS analysis after 48 hours following propidium iodine and Annexin V staining. Graphs show the percentage of G2/M arrested and apoptotic (sub-G1) cells. The data represent the mean and S.D. from at least 3 independent experiments. * $p<0.01$.

MMR-defective cell lines display resistance to a variety of therapeutic drugs including 5-fluorouracil (5-FU). The present studies have demonstrated that resistance was the result of defective incorporation of 5-FU metabolites into DNA leading to reduced damage-dependent G2/M arrest and subsequent apoptosis. The inventors examined 5-FU induced cell cycle arrest and apoptosis in Colo-320DM and SW620 cells following transfection of miR-21. The inventors used a scrambled miR as a control and compared these results to a similar transfection with a siRNA anti-MSH2 (FIG. 3). The inventors found that miR-21 over-expression decreased the percentage of sub-G1 (apoptosis) and G2/M cells following treatment with 5-FU. miR-21 transfected cells displayed reduced G2/M arrest and apoptosis similar to cells transfected with siRNA to hMSH2 (FIG. 3). The effect of miR-21 expression on 5-FU mediated apoptosis was further confirmed in Colo-320DM and SW620 by Annexin V staining (FIG. 9). A similar response was observed in isogenic Lovo cells where the hMSH2 mutation [Lovo(MSH2−)] has been complemented with the introduction of chromosome 2 [Lovo(MSH2+)] (FIG. 4). miR-21 over-expression, as well as siRNA to hMSH2 reduced sub-G1 and G2/M accumulation in Lovo(MSH2+) cells while no effects were observed in Lovo (MSH2−) cells (FIG. 4). Co-transfection of Lovo(MSH2+) and Lovo(MSH2−) cells with a plasmid encoding the full length hMSH2 cDNA promoted 5-FU induced apoptosis and cell cycle arrest. Co-transfection of the same plasmid along with miR-21 markedly reduced G2/M arrest and apoptosis (FIG. 4). Moreover, deletion of the target site in the hMSH2 cDNA rendered the message insensitive to miR-21 regulation and cells retained a normal damage-induced G2/M arrest and apoptosis. Taken as a whole, the present results are consistent with the conclusion that down-regulation of hMSH2 expression by miR-21 results in cellular resistance to 5-FU.

Example 5

Over-expression of miR-21 Induces 5-FU Resistance in a Colorectal Cancer Xenograft Model The present cellular studies showed that miR-21 inhibits 5-FU induced G2/M arrest and apoptosis by reducing the expression of hMSH2. The inventors developed a xenograft colon cancer tumor model in which the inventors generated stable clones of Lovo(MSH2+) cells that overexpressed miR-21 [Lovo(MSH2+)-miR-21] or a siRNA to hMSH2 [Lovo(MSH2+)-anti-MSH2] using a lentiviral expression system. Lovo(MSH2−) cells and Lovo(MSH2+) containing the stable insertion of an empty vector served as controls. Cells containing stable lentiviral expression were injected in the flank of nude mice (5×106 cells). When xenografts reached a palpable volume, 5-FU (50 mg/kg/day) was administered by intraperitoneal injection for 5 consecutive days per week for 2 weeks. The inventors confirmed that the expression of hMSH2 was dramatically reduced in Lovo(MSH2+) tumor xenografts expressing miR-21 or the anti-MSH2 siRNA compared to the empty vector (FIG. 4A).

Figure 5A:
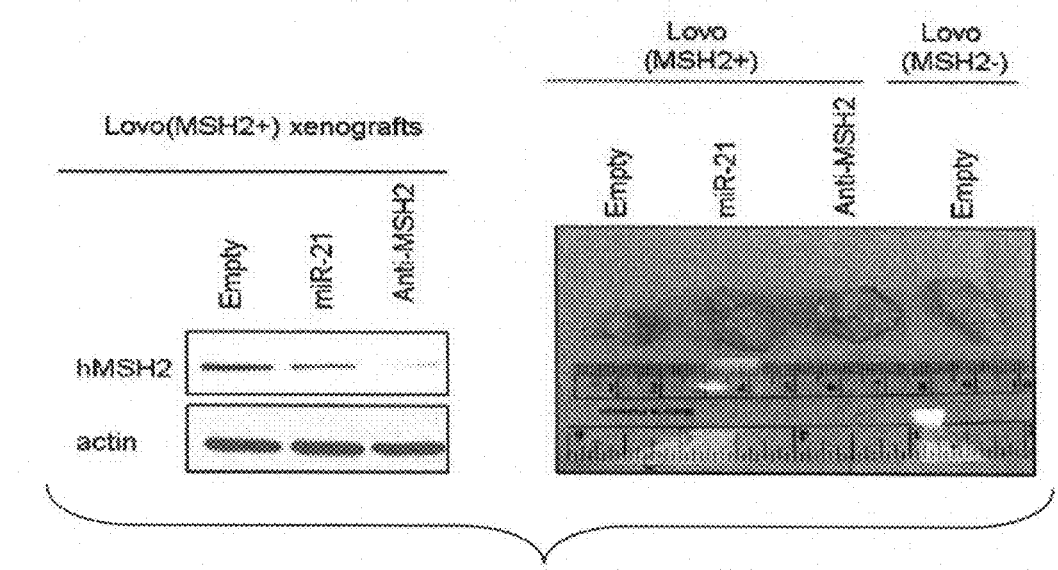
FIGS. 5A-5B. miR-21 causes resistance to 5-FU in vivo: Lovo(MSH2+) cells were stably infected with a lentiviral vector encoding for either miR-21 or siRNA anti-MSH2. As a control, Lovo(MSH2+) and Lovo(MSH2−) cells were infected with empty vectors. Nude mice were injected with Lovo (MSH2+)-Empty (n=6), Lovo(MSH2+)-miR-21 (n=6), Lovo(MSH2+)-anti-MSH2 (n=6) and Lovo(MSH2−)-Empty (n=6). When xenografts reached a palpable volume, 5-FU was administered by intraperitoneal injection for 5 consecutive days a week for 2 weeks (grey area). Tumor volume was measured before treatment and then once a week. The individual relative tumor volume (RTV) was calculated as follows RTV=Vx/V1 where Vx is the volume in cubic millimeters at a given time and V1 is the volume at the start of treatment. Results are expressed as the mean percentage of change in tumor volume for each group of mice with S.D.
Figure 5B:
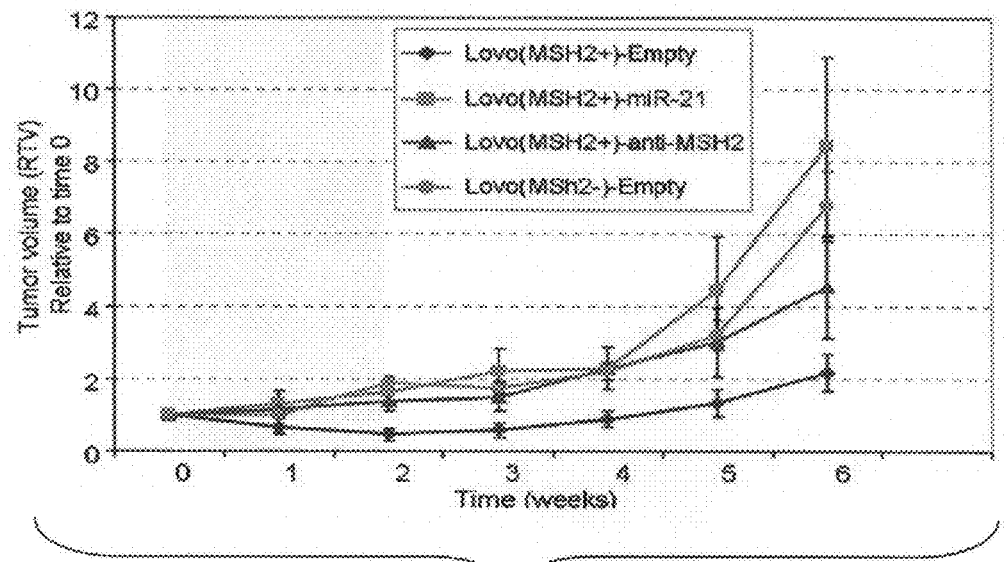

The 5-FU treatment proved to be more efficacious with Lovo(MSH2+) tumor xenografts compared to Lovo(MSH2−) tumor xenografts (FIG. 5; Table 1). The present results show that MMR-proficient cells respond better to 5-FU therapy. Importantly, stable over-expression of miR-21 [Lovo(MSH2+)-miR-21] resulted in a reduced response to 5-FU and caused a tumor growth rate comparable to those of Lovo (MSH2+) tumor cells infected with siRNA to hMSH2 [Lovo(MSH2+)-anti-MSH2] (FIG. 5; Table 1).

TABLE 1

Statistical analysis of in vivo experiments.

|  | week 1 | week 2 | week 3 | week 4 | week 5 | week 6 |
| --- | --- | --- | --- | --- | --- | --- |
| Lovo(MSH2+)-miR-21 | 0.136 | 0.008 | 0.026 | 0.040 | 0.048 | 0.035 |
| Lovo(MSH2+)-anti-MSH2 | 0.183 | 0.019 | 0.049 | 0.004 | 0.080 | 0.159 |
| Lovo(MSh2−)-Empty | 0.186 | <0.001 | 0.003 | 0.004 | 0.008 | 0.003 |

Furthermore, following 5-FU discontinuation (2 weeks) the tumor growth of the Lovo(MSH2+)-miR-21 infected cells appeared significantly greater compared to controls; showing that miR-21 overexpression enhanced cancer progression. Taken together the present results support a central role for miR-21-dependent down-regulation of the hMSH2-hMSH6 heterodimer MMR protein in 5-FU resistance.

P values are shown and have been calculated by comparing each group to the control group (Lovo(MSH2+)-Empty) by using a T-Test analysis.

Example 6

Therapeutic/Prophylactic Methods and Compositions

The invention provides methods of treatment and prophylaxis by administration to a subject an effective amount of a therapeutic antisense miR-21 of the present invention, with or without combination therapy. In a preferred aspect, the therapeutic is substantially purified. The subject is preferably an animal, including but not limited to, animals such as cows, pigs, chickens, etc., and is preferably a mammal, and most preferably human.

Various delivery systems are known and are used to administer a therapeutic of the invention, e.g., encapsulation in liposomes, microparticles, microcapsules, expression by recombinant cells, receptor-mediated endocytosis, construction of a therapeutic nucleic acid as part of a retroviral or other vector, etc. Methods of introduction include, but are not limited to, intradermal, intramuscular, intraperitoneal, intravenous, subcutaneous, intranasal, and oral routes. The compounds are administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the pharmaceutical compositions of the invention into the central nervous system by any suitable route, including intraventricular and intrathecal injection; intraventricular injection may be facilitated by an intraventricular catheter, for example, attached to a reservoir, such as an Ommaya reservoir.

In a specific embodiment, it may be desirable to administer the pharmaceutical compositions of the invention locally to the area in need of treatment; this may be achieved by, for example, and not by way of limitation, local infusion during surgery, topical application, e.g., in conjunction with a wound dressing after surgery, by injection, by means of a catheter, by means of a suppository, or by means of an implant, the implant being of a porous, non-porous, or gelatinous material, including membranes, such as sialastic membranes, or fibers. In one embodiment, administration is by direct injection at the site (or former site) of a malignant tumor or neoplastic or pre-neoplastic tissue.

In a specific embodiment where the therapeutic is a nucleic acid encoding a protein therapeutic the nucleic acid is administered in vivo to promote expression of its encoded protein, by constructing it as part of an appropriate nucleic acid expression vector and administering it so that it becomes intracellular, or coating with lipids or cell-surface receptors or transfecting agents, or by administering it in linkage to a homeobox-like peptide which is known to enter the nucleus. Alternatively, a nucleic acid therapeutic can be introduced intracellularly and incorporated within host cell DNA for expression, by homologous recombination.

The present invention also provides pharmaceutical compositions. Such compositions comprise a therapeutically effective amount of a therapeutic, and a pharmaceutically acceptable carrier or excipient. Such a carrier includes, but is not limited to, saline, buffered saline, dextrose, water, glycerol, ethanol, and combinations thereof. The carrier and composition can be sterile. The formulation will suit the mode of administration.

The composition, if desired, can also contain minor amounts of wetting or emulsifying agents, or pH buffering agents. The composition can be a liquid solution, suspension, emulsion, tablet, pill, capsule, sustained release formulation, or powder. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition also includes a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it is be dispensed with an infusion bottle containing sterile pharmaceutical grade water or saline. Where the composition is administered by injection, an ampoule of sterile water for injection or saline is provided so that the ingredients are mixed prior to administration.

The therapeutics of the invention are formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

The amount of the therapeutic of the invention which will be effective in the treatment of a particular disorder or condition will depend on the nature of the disorder or condition, and is determined by standard clinical techniques. In addition, in vitro assays may optionally be employed to help identify optimal dosage ranges. The precise dose to be employed in the formulation will also depend on the route of administration, and the seriousness of the disease or disorder, and is decided according to the judgment of the practitioner and each patient's circumstances. However, suitable dosage ranges for intravenous administration are generally about 20-500 micrograms of active compound per kilogram body weight. Suitable dosage ranges for intranasal administration are generally about 0.01 pg/kg body weight to 1 mg/kg body weight. Effective doses may be extrapolated from dose-response curves derived from in vitro or animal model test systems The invention also provides a pharmaceutical pack or kit comprising one or more containers filled with one or more of the ingredients of the pharmaceutical compositions of the invention. Optionally associated with such container(s) is a notice in the form prescribed by a governmental agency regulating the manufacture, use or sale of pharmaceuticals or biological products, which notice reflects approval by the agency of manufacture, use or sale for human administration.

Example 7

Method of Treating Cancer Patients

This example describes a method of selecting and treating patients that are likely to have a favorable response to treatments with compositions herein.

A patient diagnosed with cancer ordinarily first undergoes tissue resection with an intent to cure. Tumor samples are obtained from the portion of the tissue removed from the patient. RNA is then isolated from the tissue samples using any appropriate method for extraction of small RNAs that are well known in the art, such as by using TRIZOL™. Purified RNA is then subjected to RT-PCR using primers specific miR21 or other differentially expressed miRNAs disclosed, optionally in conjunction with genetic analysis. These assays are run to determine the expression level of the pertinent RNA in the tumor. If differentially expressed miR expression pattern is determined, especially if mutant status is ascertained, the patient is a candidate for treatment with the compositions herein.

Accordingly, the patient is treated with a therapeutically effective amount of the compositions according to methods known in the art. The dose and dosing regimen of the compositions will vary depending on a variety of factors, such as health status of the patient and the stage of the cancer. Typically, treatment is administered in many doses over time.

Example 8

Methods of Diagnosing Cancer Patients

In one particular aspect, there is provided herein a method of diagnosing whether a subject has, or is at risk for developing, cancer. The method generally includes measuring the differential miR expression pattern of the miR-21 and/or MMR protein expression compared to control. If a differential miR/MMR protein expression pattern is ascertained, the results are indicative of the subject either having, or being at risk for developing, colorectal cancer. In certain embodiments, the level of the at least one gene product is measured using Northern blot analysis. Also, in certain embodiments, the level of the at least one gene product in the test sample is less than the level of the corresponding miR gene product and/or MMR protein expression in the control sample, and/or the level of the at least one miR gene product and/or MMR protein expression in the test sample is greater than the level of the corresponding miR gene product and/or MMR protein expression in the control sample.

Example 9

Measuring miR Gene Products

The level of the at least one miR gene product can be measured by reverse transcribing RNA from a test sample obtained from the subject to provide a set of target oligodeoxynucleotides; hybridizing the target oligodeoxynucleotides to a microarray comprising miRNA-specific probe oligonucleotides to provide a hybridization profile for the test sample; and, comparing the test sample hybridization profile to a hybridization profile generated from a control sample. An alteration in the signal of at least one miRNA is indicative of the subject either having, or being at risk for developing, colorectal cancer.

Example 10

Diagnostic and Therapeutic Applications

In another aspect, there is provided herein are methods of treating a cancer in a subject, where the signal of at least one miRNA, relative to the signal generated from the control sample, is de-regulated (e.g., down-regulated and/or up-regulated).

Also provided herein are methods of diagnosing whether a subject has, or is at risk for developing, a cancer associated with one or more adverse prognostic markers in a subject, by reverse transcribing RNA from a test sample obtained from the subject to provide a set of target oligodeoxynucleotides; hybridizing the target oligodeoxynucleotides to a microarray comprising miRNA-specific probe oligonucleotides to provide a hybridization profile for the test sample; and, comparing the test sample hybridization profile to a hybridization profile generated from a control sample. An alteration in the signal is indicative of the subject either having, or being at risk for developing, the cancer.

Example 11

Kits

Any of the compositions described herein may be comprised in a kit. In a non-limiting example, reagents for isolating miRNA, labeling miRNA, and/or evaluating an miRNA population using an array are included in a kit. The kit may further include reagents for creating or synthesizing miRNA probes. The kits will thus comprise, in suitable container means, an enzyme for labeling the miRNA by incorporating labeled nucleotide or unlabeled nucleotides that are subsequently labeled. It may also include one or more buffers, such as reaction buffer, labeling buffer, washing buffer, or a hybridization buffer, compounds for preparing the miRNA probes, and components for isolating miRNA. Other kits may include components for making a nucleic acid array comprising oligonucleotides complementary to miRNAs, and thus, may include, for example, a solid support.

For any kit embodiment, including an array, there can be nucleic acid molecules that contain a sequence that is identical or complementary to all or part of any of the sequences herein.

The components of the kits may be packaged either in aqueous media or in lyophilized form. The container means of the kits will generally include at least one vial, test tube, flask, bottle, syringe or other container means, into which a component may be placed, and preferably, suitably aliquoted. Where there is more than one component in the kit (labeling reagent and label may be packaged together), the kit also will generally contain a second, third or other additional container into which the additional components may be separately placed. However, various combinations of components may be comprised in a vial. The kits of the present invention also will typically include a means for containing the nucleic acids, and any other reagent containers in close confinement for commercial sale. Such containers may include injection or blow-molded plastic containers into which the desired vials are retained.

When the components of the kit are provided in one and/or more liquid solutions, the liquid solution is an aqueous solution, with a sterile aqueous solution being one preferred solution. Other solutions that may be included in a kit are those solutions involved in isolating and/or enriching miRNA from a mixed sample.

However, the components of the kit may be provided as dried powder(s). When reagents and/or components are provided as a dry powder, the powder can be reconstituted by the addition of a suitable solvent. It is envisioned that the solvent may also be provided in another container means. The kits may also include components that facilitate isolation of the labeled miRNA. It may also include components that preserve or maintain the miRNA or that protect against its degradation. The components may be RNAse-free or protect against RNAses.

Also, the kits can generally comprise, in suitable means, distinct containers for each individual reagent or solution. The kit can also include instructions for employing the kit components as well the use of any other reagent not included in the kit. Instructions may include variations that can be implemented. It is contemplated that such reagents are embodiments of kits of the invention. Also, the kits are not limited to the particular items identified above and may include any reagent used for the manipulation or characterization of miRNA.

It is also contemplated that any embodiment discussed in the context of an miRNA array may be employed more generally in screening or profiling methods or kits of the invention. In other words, any embodiments describing what may be included in a particular array can be practiced in the context of miRNA profiling more generally and need not involve an array per se.

It is also contemplated that any kit, array or other detection technique or tool, or any method can involve profiling for any of these miRNAs. Also, it is contemplated that any embodiment discussed in the context of an miRNA array can be implemented with or without the array format in methods of the invention; in other words, any miRNA in an miRNA array may be screened or evaluated in any method of the invention according to any techniques known to those of skill in the art. The array format is not required for the screening and diagnostic methods to be implemented.

The kits for using miRNA arrays for therapeutic, prognostic, or diagnostic applications and such uses are contemplated by the inventors herein. The kits can include an miRNA array, as well as information regarding a standard or normalized miRNA profile for the miRNAs on the array. Also, in certain embodiments, control RNA or DNA can be included in the kit. The control RNA can be miRNA that can be used as a positive control for labeling and/or array analysis.

The methods and kits of the current teachings have been described broadly and generically herein. Each of the narrower species and sub-generic groupings falling within the generic disclosure also form part of the current teachings. This includes the generic description of the current teachings with a proviso or negative limitation removing any subject matter from the genus, regardless of whether or not the excised material is specifically recited herein.

Example 12

Array Preparation and Screening

Also provided herein are the preparation and use of miRNA arrays, which are ordered macroarrays or microarrays of nucleic acid molecules (probes) that are fully or nearly complementary or identical to a plurality of miRNA molecules or precursor miRNA molecules and that are positioned on a support material in a spatially separated organization. Microarrays are typically sheets of nitrocellulose or nylon upon which probes have been spotted. Microarrays position the nucleic acid probes more densely such that up to 10,000 nucleic acid molecules can be fit into a region typically 1 to 4 square centimeters.

Microarrays can be fabricated by spotting nucleic acid molecules, e.g., genes, oligonucleotides, etc., onto substrates or fabricating oligonucleotide sequences in situ on a substrate. Spotted or fabricated nucleic acid molecules can be applied in a high density matrix pattern of up to about 30 non-identical nucleic acid molecules per square centimeter or higher, e.g. up to about 100 or even 1000 per square centimeter. Microarrays typically use coated glass as the solid support, in contrast to the nitrocellulose-based material of filter arrays. By having an ordered array of miRNA-complementing nucleic acid samples, the position of each sample can be tracked and linked to the original sample.

A variety of different array devices in which a plurality of distinct nucleic acid probes are stably associated with the surface of a solid support are known to those of skill in the art. Useful substrates for arrays include nylon, glass and silicon. The arrays may vary in a number of different ways, including average probe length, sequence or types of probes, nature of bond between the probe and the array surface, e.g. covalent or non-covalent, and the like. The labeling and screening methods described herein and the arrays are not limited in its utility with respect to any parameter except that the probes detect miRNA; consequently, methods and compositions may be used with a variety of different types of miRNA arrays.

In view of the many possible embodiments to which the principles of the inventors' invention may be applied, it should be recognized that the illustrated embodiments are only preferred examples of the invention and should not be taken as a limitation on the scope of the invention. Rather, the scope of the invention is defined by the following claims. The inventors therefore claim as the inventors' invention all that comes within the scope and spirit of these claims.

What is claimed is:

1. A kit for treating colorectal cancer, wherein the cancer is characterized by reduced hMSH2 protein expression, the kit comprising: an immunohistochemistry (IHC) antibody for identifying hMSH2 expression status; and an antagonist of miR-21 in a pharmaceutically-acceptable carrier.

2. The kit of claim 1, further comprising a therapeutically effective amount of at least one pyrimidine analog.

3. The kit of claim 2, wherein the pyrimidine analog is 5-fluorouracil.

4. The kit of claim 1, wherein the antagonist of miR-21 further comprises a locked nucleic acid (LNA).

5. The kit of claim 1, wherein the patient has at least one condition selected from the group consisting of: primary pyrimidine analog-resistant colorectal cancer, acquired pyrimidine analog-resistant colorectal cancer, defective mismatch repair proteins, stage II colorectal cancer, and stage III colorectal cancer.

6. The kit of claim 1 further including instructions for using the kit for the treatment of colorectal cancer (CRC).

7. A kit for modulating hMSH2 protein expression in tumor cells of a subject, wherein the subject has been diagnosed with colorectal cancer (CRC), the kit comprising:
an effective amount of antisense miR-21 in an amount sufficient to increases hMSH2 protein expression in the subject.

8. The kit of claim 7, further comprising a therapeutically effective amount of at least one pyrimidine analog.

9. The kit of claim 8 wherein the pyrimidine analog is 5-fluorouracil.

10. The kit of claim 7, wherein the antisense miR-21 further comprises a locked nucleic acid (LNA).

11. The kit of claim 7, wherein the patient has at least one condition selected from the group consisting of: primary pyrimidine analog-resistant colorectal cancer, acquired pyrimidine analog-resistant colorectal cancer, defective mismatch repair proteins, stage II colorectal cancer, and stage III colorectal cancer.

12. The kit of claim 7, further including instructions for using the kit for the treatment of colorectal cancer (CRC).

* * * * *